(12) United States Patent
Hayakawa et al.

(10) Patent No.: US 11,970,438 B2
(45) Date of Patent: Apr. 30, 2024

(54) COMPOUND, INK, RESIST COMPOSITION FOR COLOR FILTER, SHEET FOR HEAT-SENSITIVE TRANSFER RECORDING, AND TONER

(71) Applicant: CANON KABUSHIKI KAISHA, Tokyo (JP)

(72) Inventors: Ai Hayakawa, Kanagawa (JP); Koromo Shirota, Kanagawa (JP); Taichi Shintou, Saitama (JP); Tsuyoshi Santo, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 457 days.

(21) Appl. No.: 17/231,228

(22) Filed: Apr. 15, 2021

(65) Prior Publication Data

US 2021/0230109 A1 Jul. 29, 2021

Related U.S. Application Data

(63) Continuation of application No. PCT/JP2019/041296, filed on Oct. 21, 2019.

(30) Foreign Application Priority Data

Oct. 23, 2018 (JP) .................................. 2018-199119

(51) Int. Cl.
| | | |
|---|---|---|
| C07C 309/46 | (2006.01) | |
| C07C 211/56 | (2006.01) | |
| C09D 11/037 | (2014.01) | |
| G03F 7/00 | (2006.01) | |
| G03G 9/087 | (2006.01) | |
| G03G 9/09 | (2006.01) | |

(52) U.S. Cl.
CPC .......... C07C 309/46 (2013.01); C07C 211/56 (2013.01); *C09D 11/037* (2013.01); *G03F 7/0007* (2013.01); *G03G 9/08784* (2013.01); *G03G 9/0906* (2013.01)

(58) Field of Classification Search
CPC ... C07C 211/56; C07C 309/46; C07C 311/39; C09D 11/037; G03F 7/0007; G03F 7/0045; G03F 7/0226; G03F 7/027; G03F 7/031; G03F 7/033; G03F 7/038; G03F 7/105; G03G 9/08784; G03G 9/0906; G03G 9/0924; G03G 9/0926; B41M 5/385; C09B 11/18; G02B 5/20
See application file for complete search history.

(56) References Cited

U.S. PATENT DOCUMENTS

| | | |
|---|---|---|
| 4,664,671 A | 5/1987 | Gregory |
| 7,407,540 B2 | 8/2008 | Yamagishi et al. |
| 10,351,526 B2 | 7/2019 | Ishiwata et al. |
| 10,358,567 B2 | 7/2019 | Tani et al. |
| 10,647,142 B2 | 5/2020 | Shintou et al. |
| 2017/0247557 A1* | 8/2017 | Tani ...................... C07C 309/58 |
| 2020/0283633 A1 | 9/2020 | Hayakawa et al. |

FOREIGN PATENT DOCUMENTS

| | | |
|---|---|---|
| JP | 61-141593 A | 6/1986 |
| JP | 2-026781 A | 1/1990 |
| JP | 2006-257410 A | 9/2006 |
| JP | 2011-133805 A | 7/2011 |
| JP | 2013-120267 A | 6/2013 |
| JP | 2013-148889 A | 8/2013 |
| JP | 2016-40593 A | 3/2016 |
| JP | 2017-155216 A | 9/2017 |
| JP | 2018-81210 A | 5/2018 |
| JP | 2018-099880 A | 6/2018 |

(Continued)

OTHER PUBLICATIONS

JP2018104508 translated (Year: 2018).*

(Continued)

*Primary Examiner* — Yevgeny Valenrod
*Assistant Examiner* — Blaine G Doletski
(74) *Attorney, Agent, or Firm* — Venable LLP

(57) ABSTRACT

There is provided a compound having a structure represented by the following Formula (1),

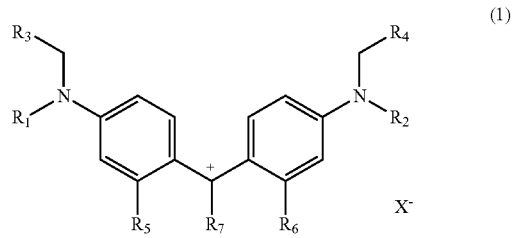

in Formula (1), $R_1$ and $R_2$ each independently represent a phenyl group having a substituent or an unsubstituted phenyl group, $R_3$ and $R_4$ each independently represent a C2-C12 alkyl group having a substituent or an unsubstituted C2-C12 alkyl group, a cyano group, a trifluoromethyl group, or a halogen atom, $R_5$ and $R_6$ each independently represent a hydrogen atom or an alkyl group, $R_7$ represents a phenyl group having a substituent, an unsubstituted phenyl group, or a heteroaromatic group having a specific structure, and $X^-$ represents an anion, and in a case where at least one anionic substituent is included in a molecule, $X^-$ may not be present.

8 Claims, No Drawings

(56) References Cited

FOREIGN PATENT DOCUMENTS

| JP | 2018-104508 A | | 7/2018 |
|---|---|---|---|
| JP | 2018104508 | * | 7/2018 |
| JP | 2019-99795 A | | 6/2019 |
| WO | WO2017/056372 | * | 4/2017 |
| WO | 2020/085298 A1 | | 4/2020 |

OTHER PUBLICATIONS

International Preliminary Report on Patentability in International Application No. PCT/JP2019/041296 (dated May 2021).
Notice of Reasons for Refusal in Japanese Application No. 2019-188540 (dated Jun. 2023).
C. de Diego et al., "Heteroaromatic Analogues of Triarylmethane Dyes," 28 Chemica Scripta 403-409 (1988).
International Search Report in International Application No. PCT/JP2019/041296 (dated Dec. 2019).
Notice of Reasons for Refusal in Japanese Application No. 2019-188540 (dated Oct. 2023).

* cited by examiner

COMPOUND, INK, RESIST COMPOSITION FOR COLOR FILTER, SHEET FOR HEAT-SENSITIVE TRANSFER RECORDING, AND TONER

CROSS-REFERENCE TO RELATED APPLICATIONS

This application is a Continuation of International Patent Application No. PCT/JP2019/041296, filed Oct. 21, 2019, which claims the benefit of Japanese Patent Application No. 2018-199119, filed Oct. 23, 2018, both of which are hereby incorporated by reference herein in their entirety.

BACKGROUND OF THE INVENTION

Field of the Invention

The present invention relates to a compound, and to an ink, a resist composition for a color filter, a sheet for heat-sensitive transfer recording, and a toner that are obtained by using the compound.

Description of the Related Art

In a color display using a liquid crystal, a color filter is used. The color filter is essential to display color of a liquid crystal display and is an important component determining performance of the liquid crystal display. As a method of producing a color filter according to the related art, a dying method, a printing method, an ink jet method, and a photoresist method have been known. Among them, a photoresist method has been primarily used because the photoresist method facilitates a control of spectral characteristics and color reproducibility, and implements high resolution and higher precision patterning.

In the production of a color filter by a photoresist method, in general, a pigment has been used as a coloring agent. However, a color filter using a pigment has many problems, such as depolarization (destruction of polarization), reduction in a contrast ratio of color display of a liquid crystal display, reduction in brightness of a color filter, and reduction in storage stability with respect to an organic solvent or a polymer. Therefore, a method of producing a color filter using a dye as a coloring agent has been spotlighted. Japanese Patent Application Laid-Open No. 2018-81210 discloses a color filter using a triphenylmethane-based colorant as a coloring agent.

In addition, in recent years, with the spread of a portable color display device, a demand for easy color printing of photos captured and processed by using the device and documents prepared by using the device has been rapidly increased.

As a color printing method, an electrophotographic method, an ink jet method, a heat-sensitive transfer recording method, and the like have been known. Among them, a heat-sensitive transfer recording method is excellent as a method by which printing can be easily performed regardless of a surrounding environment, because the heat-sensitive transfer recording method enables printing to be performed by a dry process and allows a printer to be downsized and to have excellent portability. In the heat-sensitive transfer recording method, a dye contained in a transfer sheet and an ink composition for a transfer sheet is a very important material because the dye affects a speed of transfer recording and an image quality and storage stability of a recorded matter. Japanese Patent Application Laid-Open No. S61-141593 discloses an example in which a heat-sensitive recorded matter with high brightness is obtained by using a triphenylmethane-based colorant as a colorant used in a heat-sensitive transfer recording method.

In addition, in the field of the color toner used in the electrophotographic method, it is required to suppress image density unevenness caused by oxidation on a surface of a photosensitive body and image defects due to scratches on the surface of the photosensitive body caused by adhesion of carriers in accordance with a residual potential on the surface of the photosensitive body. Japanese Patent Application Laid-Open No. 2011-133805 discloses an example in which a triphenylmethane-based colorant is used as an antioxidant for such suppression.

Furthermore, digital textile printing using an ink jet method or an electrophotographic method has been spread in the market as a method capable of providing a textile printing product at low energy and low cost. However, C. I. Acid Blue 7 or C. I. Acid Blue 9 is used for digital textile printing as a triphenylmethane-based colorant; however, there is a problem in that light fastness is not sufficient.

Triphenylmethane-based dyes described in the above-described literatures have low light fastness, easily aggregate, and have poor storage stability.

An object of the present invention is to provide a compound having high light fastness and excellent storage stability. In addition, an object of the present invention is to provide an ink, a resist composition for a color filter, a sheet for heat-sensitive transfer recording, and a toner that have high light fastness and excellent storage stability by using the compound.

SUMMARY OF THE INVENTION

According to the present invention, there is provided a compound having a structure represented by the following Formula (1).

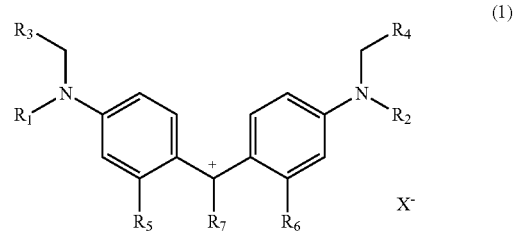

In Formula (1), $R_1$ and $R_2$ each independently represent a phenyl group having a substituent or an unsubstituted phenyl group, $R_3$ and $R_4$ each independently represent a C2-C12 alkyl group having a substituent or an unsubstituted C2-C12 alkyl group, a cyano group, a trifluoromethyl group, or a halogen atom, $R_5$ and $R_6$ each independently represent a hydrogen atom or an alkyl group, $R_7$ represents a structure represented by the following Formula (2) or (3), $$\begin{matrix} & (2) \\ R_9 \underset{\phantom{-}}{\overset{\phantom{-}}{\bigodot}} R_8 \end{matrix}$$

$$\begin{matrix} & (3) \\ R_{10}\text{-}N\underset{\phantom{-}}{\overset{\phantom{-}}{\bigodot}} R_{11} \\ & R_{12} \end{matrix}$$

in Formula (2), $R_8$ represents a $-SO_3^-$ group, an alkoxysulfonyl group, a sulfonic acid amide group, a halogen atom, a perfluoroalkyl group, or a nitro group, and $R_9$ represents a hydrogen atom or a halogen atom, and in Formula (3), $R_{10}$ to $R_{12}$ each independently represent a hydrogen atom, an alkyl group, or an aryl group having a substituent or an unsubstituted aryl group, and $X^-$ represents an anion, and in a case where at least one anionic substituent is included in a molecule, $X^-$ may not be present.

In addition, according to the present invention, there is provided an ink containing a medium and a compound present in a dissolved or dispersed state in the medium, in which the compound is the compound described above.

In addition, according to the present invention, there is provided a resist composition for a color filter containing the compound described above.

In addition, according to the present invention, there is provided a sheet for heat-sensitive transfer recording including a substrate and a coloring material layer formed on the substrate, in which the coloring material layer contains the compound described above.

In addition, according to the present invention, there is provided a toner containing a binder resin and a coloring agent, in which the coloring agent contains the compound described above.

Further features of the present invention will become apparent from the following description of exemplary embodiments.

DESCRIPTION OF THE EMBODIMENTS

Hereinafter, embodiments of the present invention will be described in detail, but the technical scope of the present invention is not limited thereto.

The present inventors conducted intensive studies in order to solve the above problems, and as a result, have found that a compound having a structure represented by the following Formula (1) has high light fastness and excellent storage stability.

In Formula (1), $R_1$ and $R_2$ each independently represent a phenyl group having a substituent or an unsubstituted phenyl group, $R_3$ and $R_4$ each independently represent a C2-C12 alkyl group having a substituent or an unsubstituted C2-C12 alkyl group, a cyano group, a trifluoromethyl group, or a halogen atom, $R_5$ and $R_6$ each independently represent a hydrogen atom or an alkyl group, $R_7$ represents a structure represented by the following Formula (2) or (3), in Formula (2), $R_8$ represents a $-SO_3^-$ group, an alkoxysulfonyl group, a sulfonic acid amide group, a halogen atom, a perfluoroalkyl group, or a nitro group, and $R_9$ represents a hydrogen atom or a halogen atom, and in Formula (3), $R_{10}$ to $R_{12}$ each independently represent a hydrogen atom, an alkyl group, or an aryl group having a substituent or an unsubstituted aryl group, and $X^-$ represents an anion, and in a case where at least one anionic substituent is included in a molecule, $X^-$ may not be present.

It was determined in comparative examples described below that even in a case where the compound has the same basic structure as that of Formula (1), when $R_1$ to $R_4$ in Formula (1) are substituents other than $R_1$ to $R_4$, solubility of the compound in a solvent is lowered, resulting in not only a high possibility of condensation of the compound but also low light fastness.

On the other hand, in the case of the compound of the present invention, $R_1$ and $R_2$ each independently represent a phenyl group having a substituent or an unsubstituted phenyl group.

$R_3$ and $R_4$ each independently represent a C2-C12 alkyl group having a substituent or an unsubstituted C2-C12 alkyl group, a cyano group, a trifluoromethyl group, or a halogen atom. One methylene group is present between a nitrogen atom and $R_3$, and one methylene group is present between a nitrogen atom and $R_4$.

Since $R_1$ and $R_3$ and $R_2$ and $R_4$ have asymmetrical and bulky structures, respectively, three substituents substituted at the N-position form a sterically twisted structure. Therefore, it is considered that an interaction between the compounds in the molecule or between the molecules is suppressed and aggregation is thus controlled. In addition, it is considered that when the phenyl group having the substituent or the unsubstituted phenyl group as $R_1$ or $R_2$ directly binds to a nitrogen atom, a charge is delocalized, and a compound having stability and high light fastness is thus formed.

In addition, it was found that it is possible to obtain an ink, a resist composition for a color filter, a color filter, a sheet for heat-sensitive transfer recording, and a toner that have high light fastness and excellent storage stability by using the compound represented by Formula (1).

First, the compound represented by Formula (1) will be described.

In Formula (1), the substituent in the "phenyl group having the substituent" in $R_1$ or $R_2$ is not particularly limited, but examples thereof can include the following: a linear, branched, or cyclic alkyl group having 1 to 20 carbon atoms, an alkoxy group, a cyano group, a halogen atom, a sulfo group ($-SO_3H$), a sulfonic acid ester group, a sulfonamide group, a sulfonate group, a benzenesulfonyl group, and a trifluoromethanesulfonyl group.

In Formula (1), the alkyl group substituted for the phenyl group in $R_1$ or $R_2$ is not particularly limited, but examples thereof can include the following: a methyl group, an ethyl group, an n-propyl group, an iso-propyl group, an n-butyl group, a sec-butyl group, a tert-butyl group, an n-hexyl group, a cyclohexyl group, a 2-ethylhexyl group, an octyl group, a decyl group, and a dodecyl group.

Among them, a methyl group, an n-butyl group, an n-hexyl group, a 2-ethylhexyl group, an octyl group, or a decyl group is preferable in terms of excellent light fastness and storage stability.

In Formula (1), the alkoxy group substituted for the phenyl group in $R_1$ or $R_2$ is not particularly limited, but examples thereof can include the following: a methoxy group, an ethoxy group, a propoxy group, an n-butoxy group, a t-butoxy group, a hexyloxy group, a 2-ethylhexyloxy group, an octyloxy group, a decyloxy group, and a dodecyloxy group.

Among them, an n-butoxy group, a hexyloxy group, a 2-ethylhexyloxy group, an octyloxy group, or a decyloxy group is preferable in terms of excellent light fastness and storage stability.

In Formula (1), the halogen atom substituted for the phenyl group in $R_1$ or $R_2$ is not particularly limited, but examples thereof can include a fluorine atom, a chlorine atom, a bromine atom, and an iodine atom. Among them, a fluorine atom or a chlorine atom is preferable in terms of excellent light fastness and storage stability.

In Formula (1), the sulfonic acid ester group substituted for the phenyl group in $R_1$ or $R_2$ is not particularly limited, but examples thereof can include the following: a methyl sulfonate group, an ethyl sulfonate group, a propyl sulfonate group, a butyl sulfonate group, a hexyl sulfonate group, and an octyl sulfonate group. Among them, a butyl sulfonate group or a hexyl sulfonate group is preferable in terms of excellent light fastness and storage stability.

In Formula (1), the sulfonamide group substituted for the phenyl group in $R_1$ or $R_2$ is not particularly limited, but examples thereof can include the following: an N-methylsulfonamide group, an N,N-dimethylsulfonamide group, an N-ethylsulfonamide group, an N,N-diethylsulfonamide group, an N-propylsulfonamide group, an N,N-dipropylsulfonamide group, an N-butylsulfonamide group, an N,N-dibutylsulfonamide group, an N-pentylsulfonamide group, an N,N-dipentylsulfonamide group, an N-hexylsulfonamide group, an N,N-dihexylsulfonamide group, an N-octylsulfonamide group, an N,N-dioctylsulfonamide group, an N-(2-ethylhexyl)sulfonamide group, an N,N-bis(2-ethylhexyl)sulfonamide group, an N-(1-methylhexyl)sulfonamide group, an N-(1-methylheptyl)sulfonamide group, an N-methyl-N-butylsulfonamide group, an N-methyl-N-pentylsulfonamide group, an N-methyl-N-hexylsulfonamide group, an N-methyl-N-octylsulfonamide group, an N-phenylsulfonamide group, an N-(p-methylphenyl)sulfonamide group, an N-pyrrolidylsulfonyl group, and an N-piperidylsulfonyl group.

Among them, in terms of excellent light fastness and storage stability, preferred sulfonamide groups are as follows: an N,N-dibutylsulfonamide group, an N,N-dipentylsulfonamide group, an N,N-dihexylsulfonamide group, an N,N-dioctylsulfonamide group, and an N,N-bis(2-ethylhexyl)sulfonamide group.

In Formula (1), the sulfonate group substituted for the phenyl group in $R_1$ or $R_2$ is not particularly limited, but examples thereof can include a lithium sulfonic acid salt, a sodium sulfonic acid salt, and a potassium sulfonic acid salt.

In Formula (1), the unsubstituted alkyl group in $R_3$ or $R_4$ is not particularly limited, but in terms of obtaining a compound having excellent light fastness and storage stability, examples thereof can include the following: an ethyl group, an n-propyl group, an iso-propyl group, an n-butyl group, a sec-butyl group, a tert-butyl group, an n-hexyl group, a cyclohexyl group, a 2-ethylhexyl group, a heptyl group, an octyl group, a decyl group, and a dodecyl group.

In Formula (1), the substituent for the alkyl group having the substituent in $R_3$ or $R_4$ is not particularly limited, but a methoxy group, a bromine atom, a chlorine atom, a fluorine atom, a cyano group, a trifluoromethyl group, or the like is preferable in terms of obtaining a compound having excellent light fastness and storage stability.

In Formula (1), the halogen atom in $R_3$ or $R_4$ is not particularly limited, but examples thereof can include a bromine atom, a chlorine atom, a fluorine atom, and an iodine atom. Among them, a chlorine atom or an iodine atom is preferable in terms of obtaining a compound having excellent light fastness and storage stability.

In Formula (1), the alkyl group in $R_5$ or $R_6$ is not particularly limited, but examples thereof can include a methyl group, an ethyl group, an n-propyl group, an iso-propyl group, and an n-butyl group. Among them, a methyl group or an ethyl group is preferable in terms of obtaining a compound having excellent light fastness and storage stability.

In Formula (1), $R_7$ has a structure represented by the following Formula (2) or (3). When $R_7$ has such a structure, light fastness and storage stability are excellent.

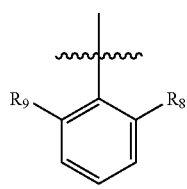
(2)

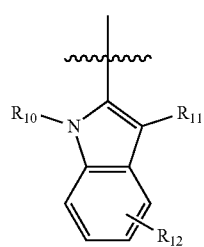
(3)

In Formula (2), $R_8$ represents a $-SO_3^-$ group, an alkoxysulfonyl group ($-SO_3R$ group), a sulfonic acid amide group ($-SO_2NRR$ group), a halogen atom, a perfluoroalkyl group, or a nitro group, and $R_9$ represents a hydrogen atom or a halogen atom.

In Formula (2), the halogen atoms in $R_8$ and $R_9$ are not particularly limited, but examples thereof can include a fluorine atom, a chlorine atom, a bromine atom, and an iodine atom. The perfluoroalkyl group in $R_8$ is not particularly limited, but examples thereof can include a trifluoromethyl group, a perfluoroethyl group, and a perfluoropropyl group.

In Formula (3), $R_{10}$ to $R_{12}$ each independently represent a hydrogen atom, an alkyl group, or an aryl group having a substituent or an unsubstituted aryl group.

In Formula (3), examples of the alkyl group in each of $R_{10}$ to $R_{12}$ can include the same substituents as those exemplified as the alkyl group in $R_1$ and $R_2$ in Formula (1).

In Formula (3), the aryl group having the substituent or the unsubstituted aryl group in each of $R_{10}$ to $R_{12}$ is not particularly limited, but an example thereof can include a phenyl group. The substituent for the aryl group is not particularly limited, but examples thereof can include a methyl group, an ethyl group, a methoxy group, and a cyano group.

In Formula (1), the anion of $X^-$ is not particularly limited, but examples thereof can include the following: a fluorine ion, a chlorine ion, a bromine ion, an iodine ion, a cyanide ion, a nitrate ion, a benzenesulfonate ion, p-toluene sulfonate ion, a methyl sulfate ion, an ethyl sulfate ion, a propyl sulfate ion, a tetrafluoroborate ion, a tetraphenylborate ion, a benzenesulfinate ion, an acetate ion, a trifluoroacetate ion, a propionate ion, a benzoate ion, an oxalate ion, a succinate ion, a malonate ion, an oleate ion, a stearate ion, a citrate ion, a picolinate ion, a monohydrogen diphosphate ion, a dihydrogen diphosphate ion, a pentafluoropropionate ion, a chlorosulfonate ion, a fluorosulfonate ion, a perchlorate anion, a trifluoromethanesulfonyl anion, a bis(trifluoromethanesulfonyl)imide anion, a naphthalenesulfonyl ion, a naphthalene disulfonate ion, a tristrifluoromethanesulfonyl methide anion, a tetraarylborate anion, and a sulfate anion.

In Formula (1), $R_7$ is particularly preferably a group represented by the following Formula (4).

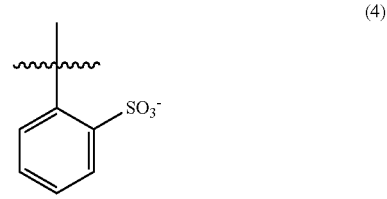
(4)

Preferred examples of the compound represented by Formula (1) can include the following compounds (A1) to (A102), but the present invention is not limited to the following compounds.

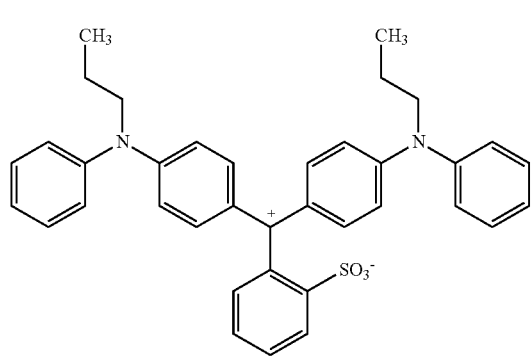
(A1)

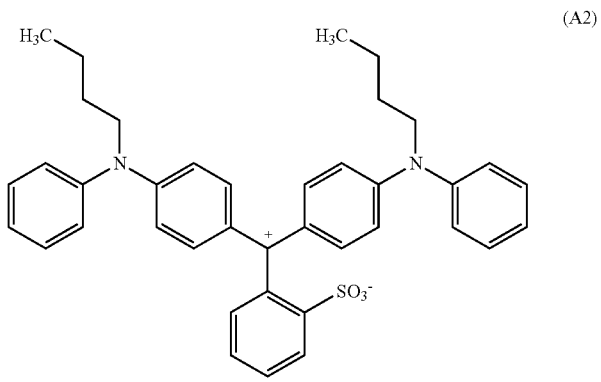
(A2)

-continued
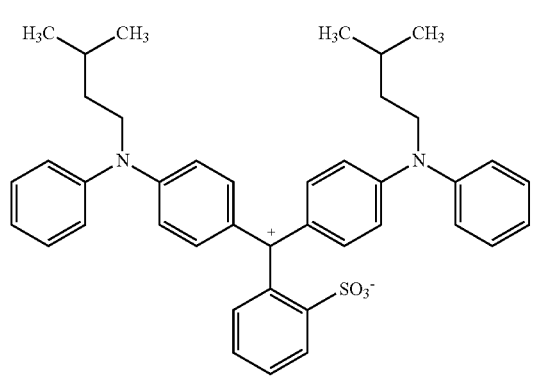
(A3)
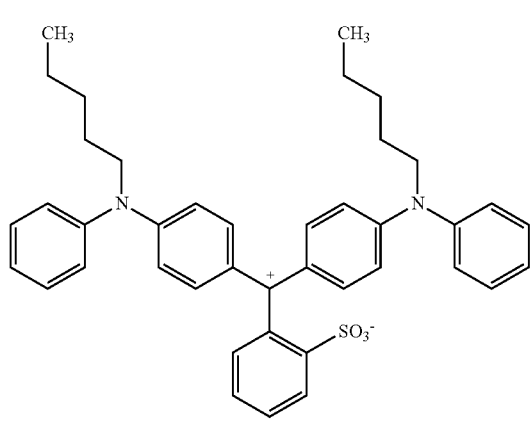
(A4)
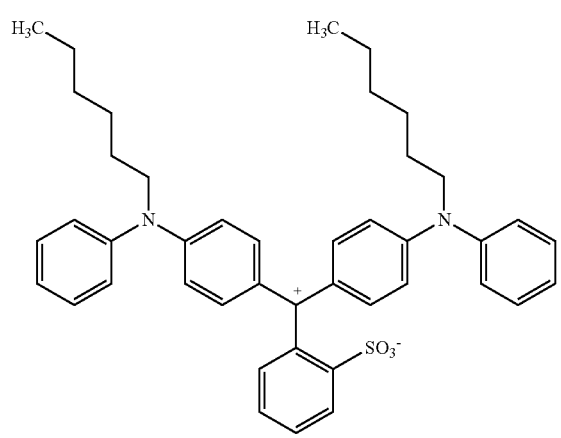
(A5)
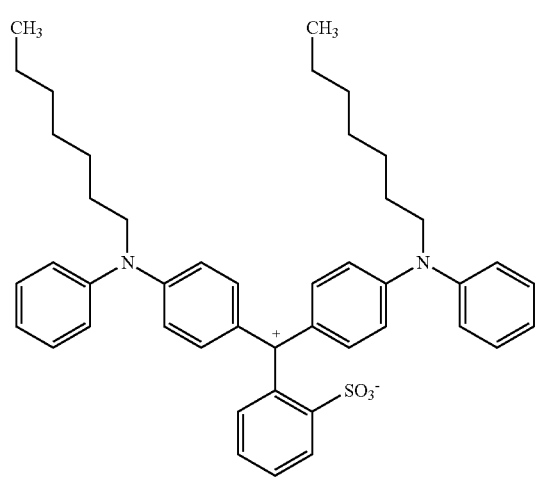
(A6)
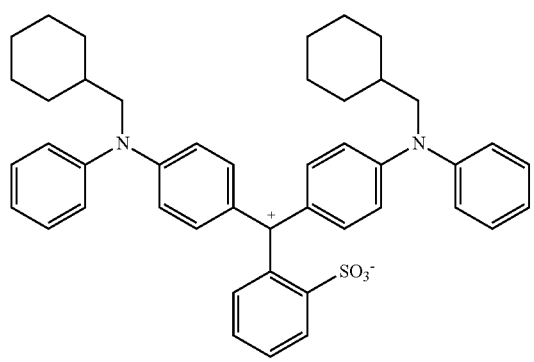
(A7)
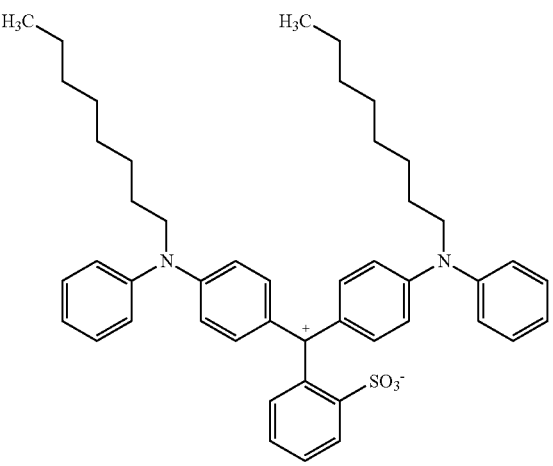
(A8)

-continued
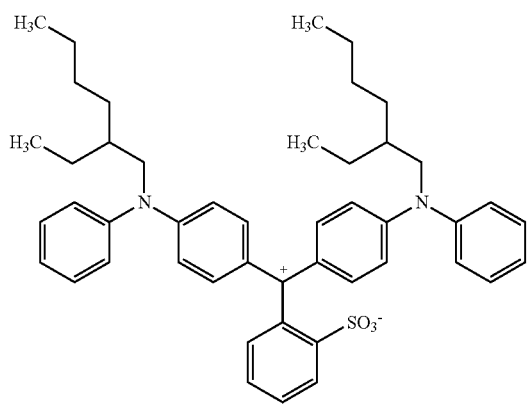
(A9)
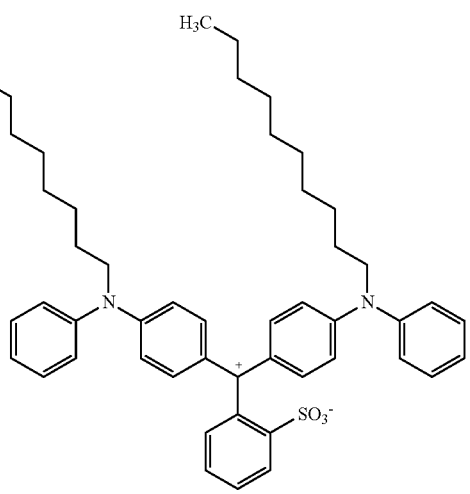
(A10)
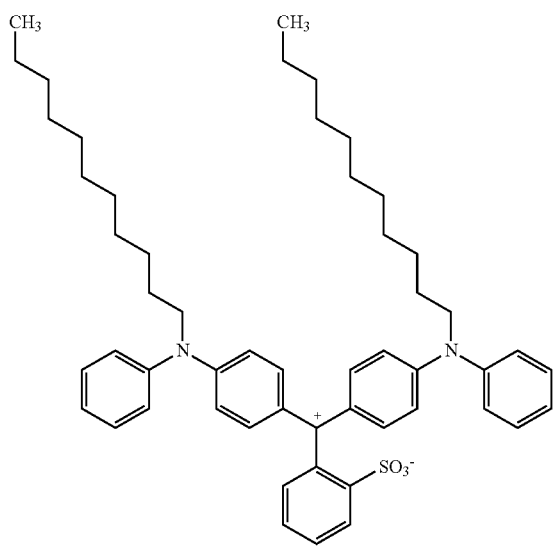
(A11)
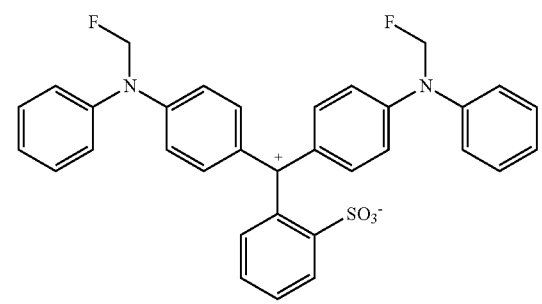
(A12)
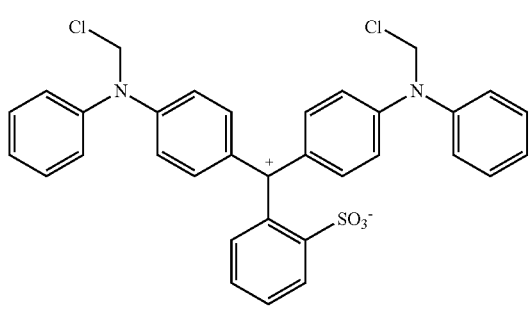
(A13)
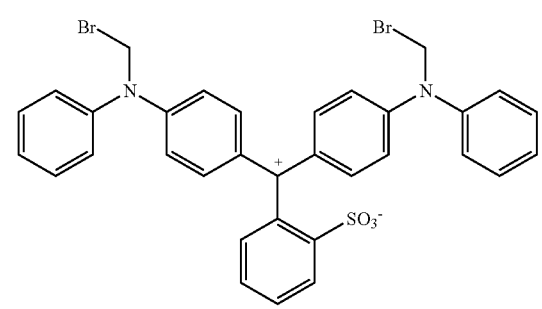
(A14)
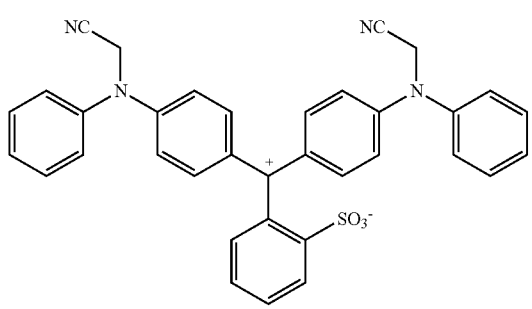
(A15)
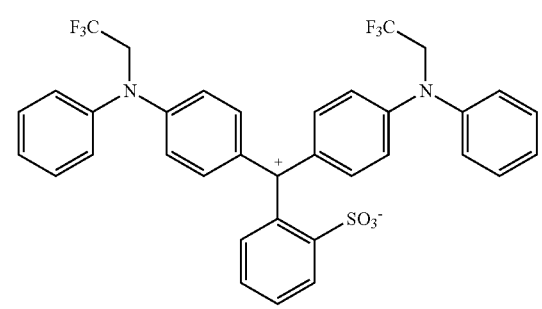
(A16)

-continued
(A17)
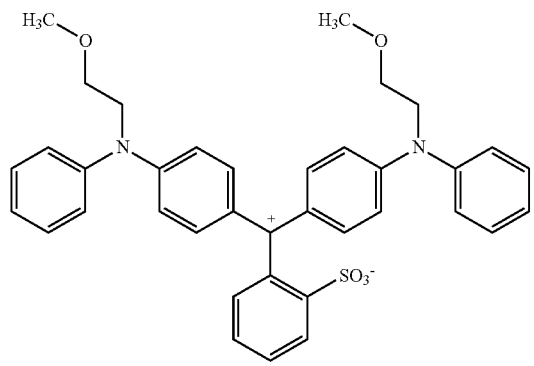
(A18)
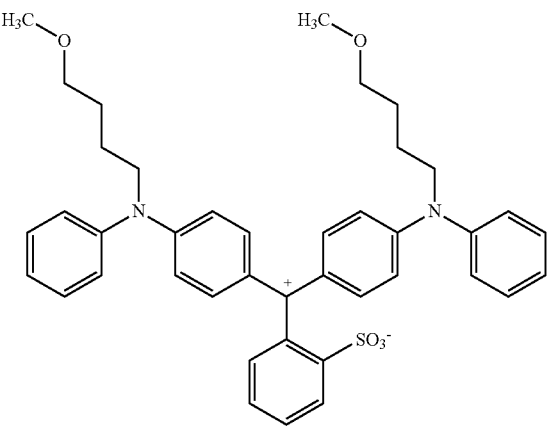
(A19)
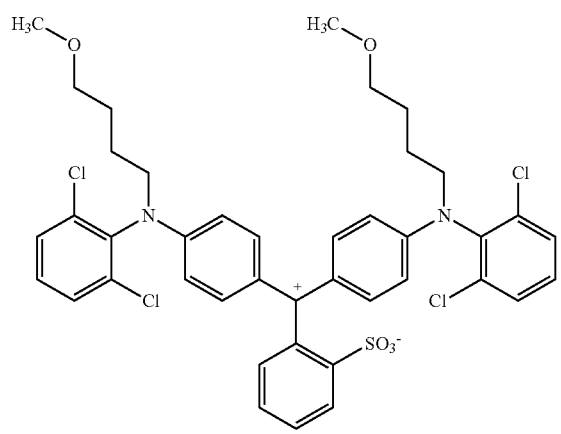
(A20)
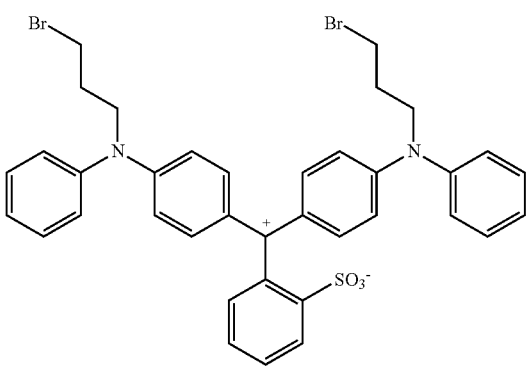
(A21)
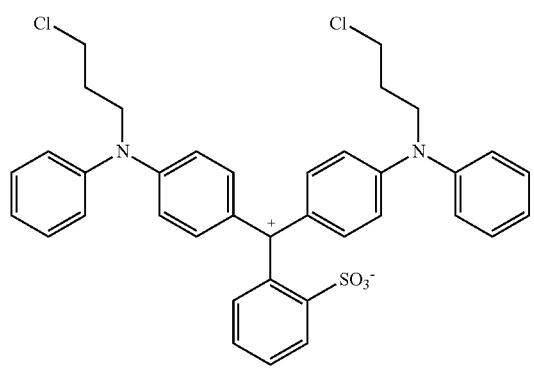
(A22)
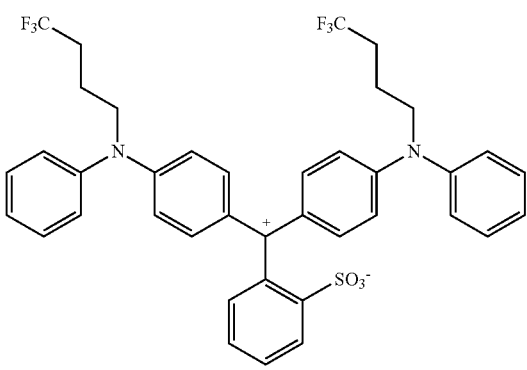
(A23)
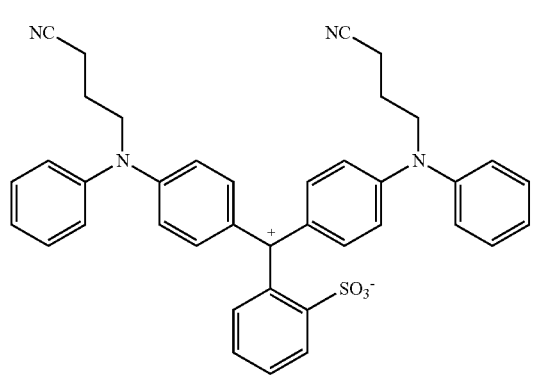
(A24)
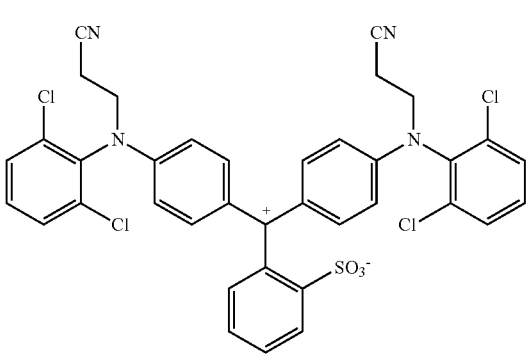

(A25) 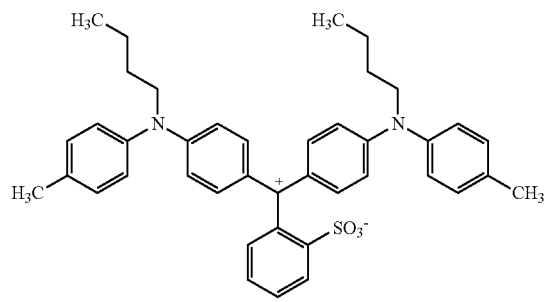
(A26) 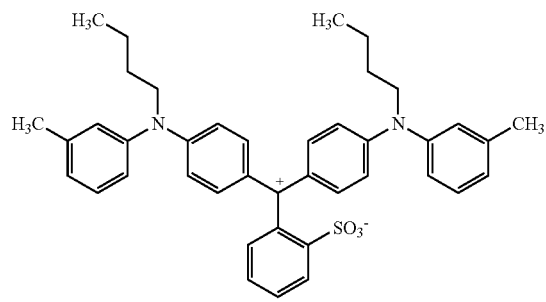
(A27) 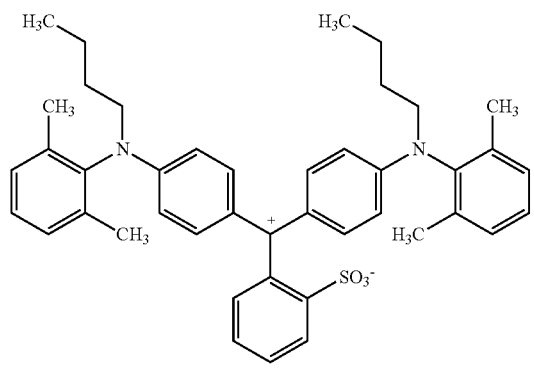
(A28) 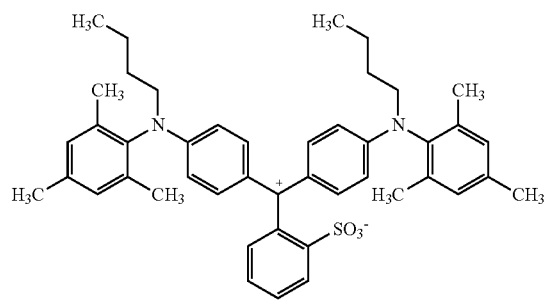
(A29) 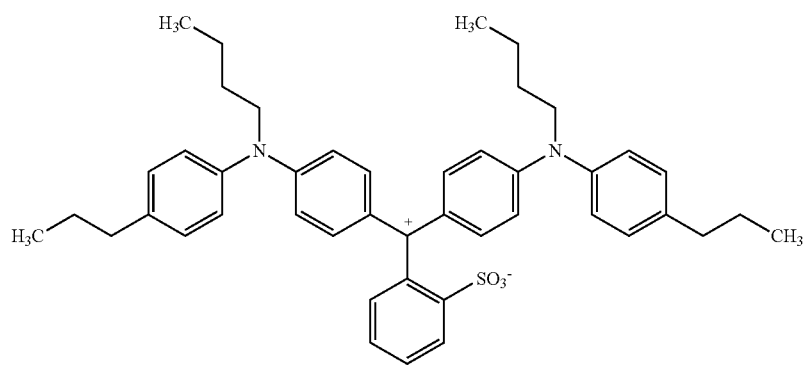
(A30) 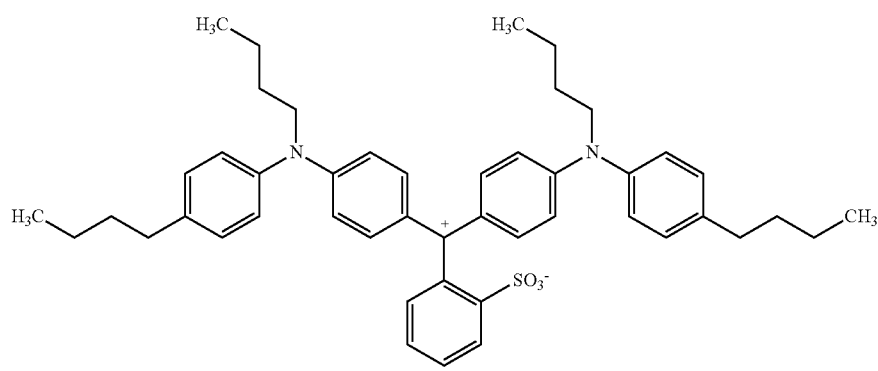

-continued
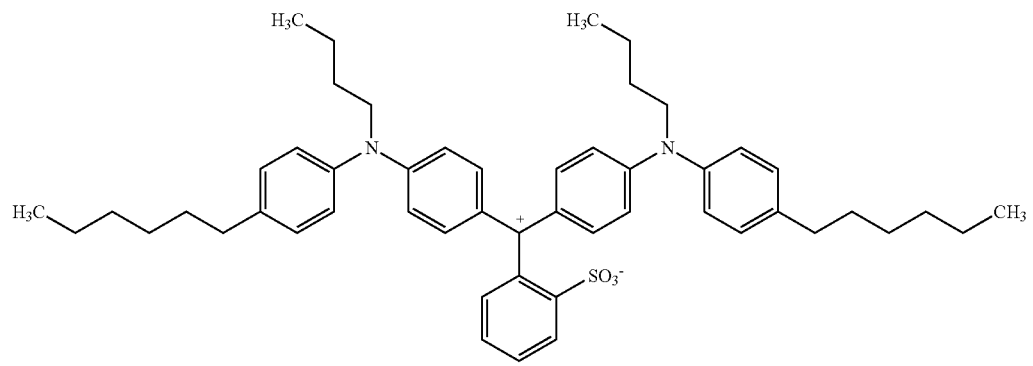
(A31)
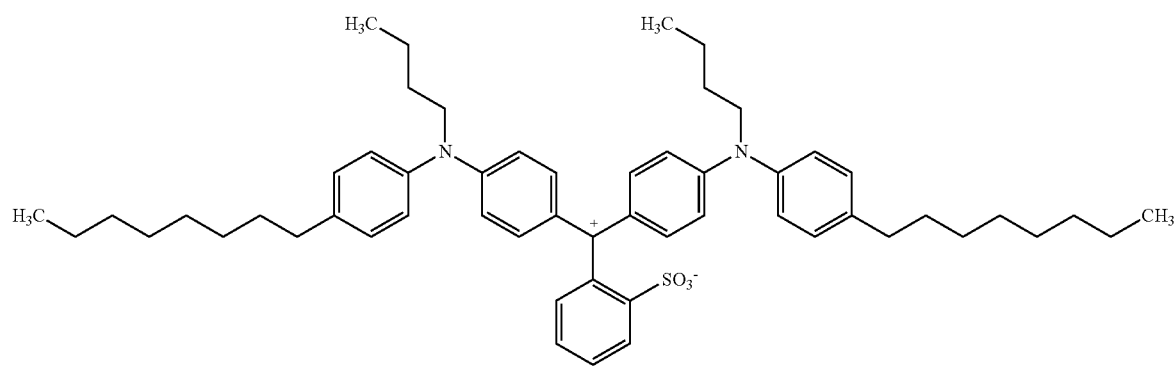
(A32)
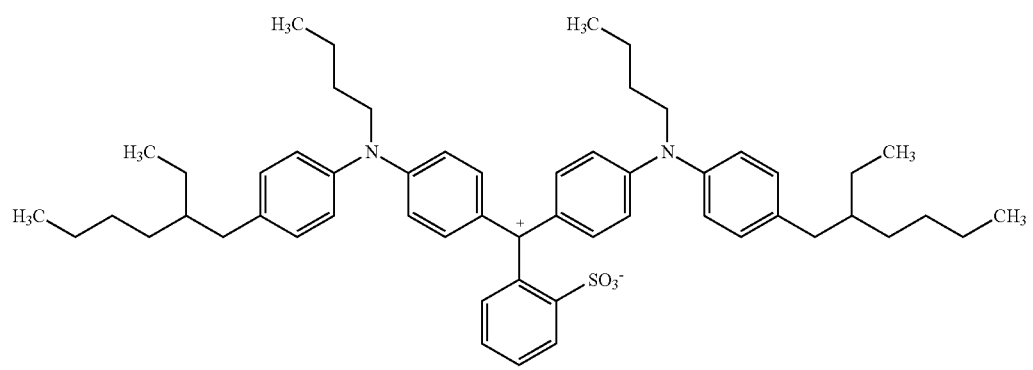
(A33)
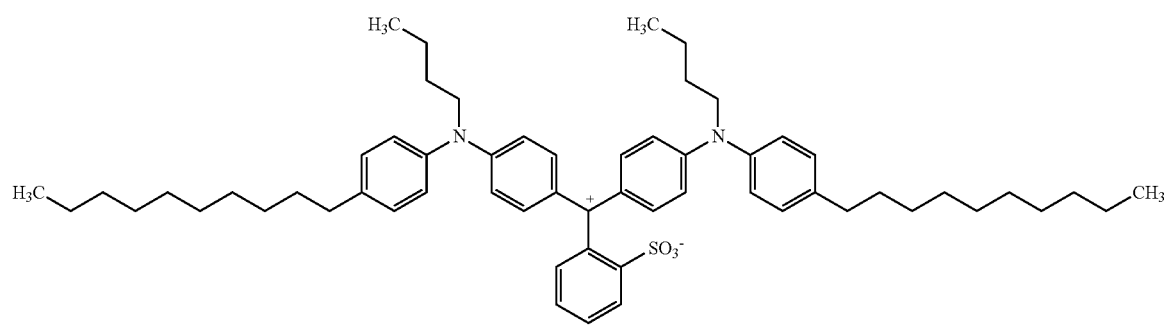
(A34)

-continued
(A35)
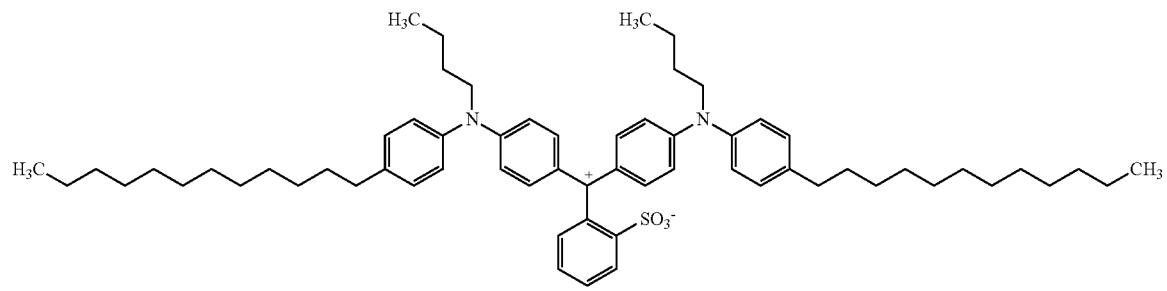
(A36)
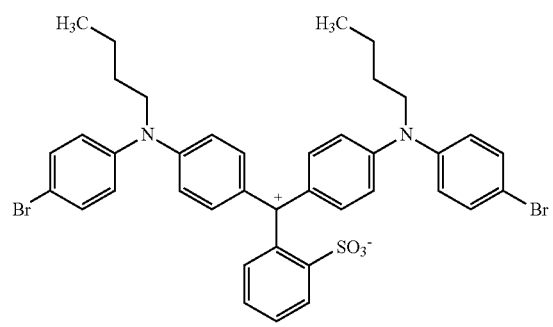
(A37)
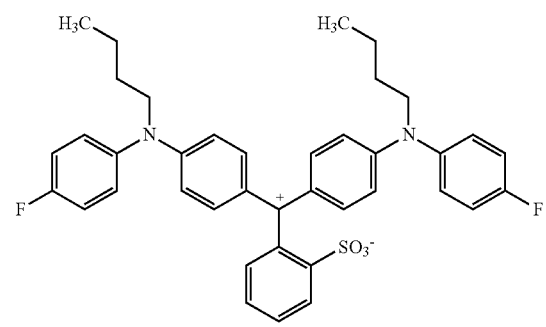
(A38)
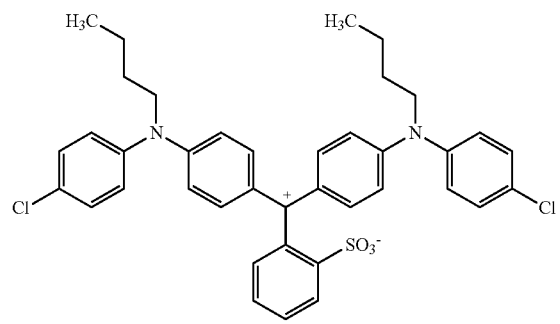
(A39)
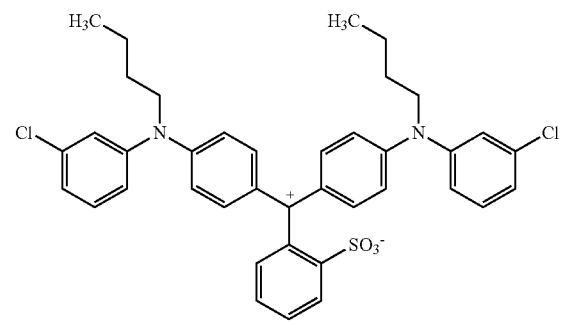
(A40)
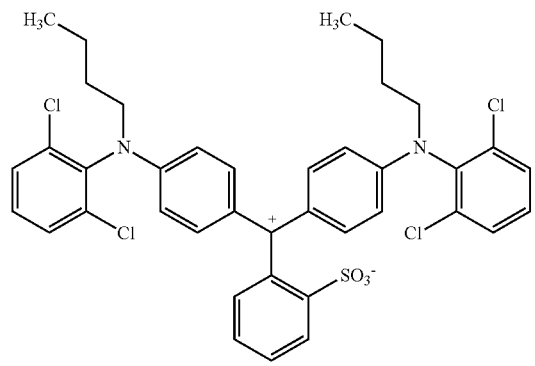
(A41)
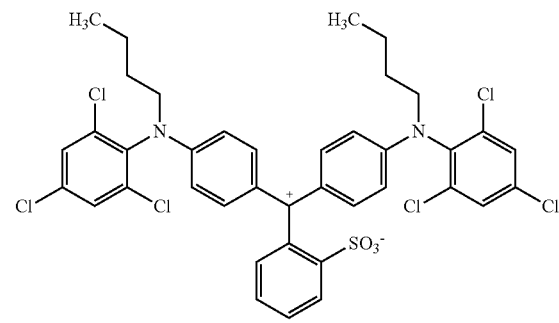

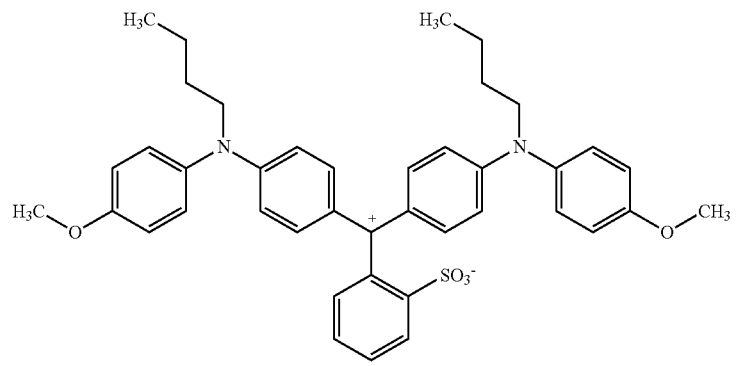
(A42)
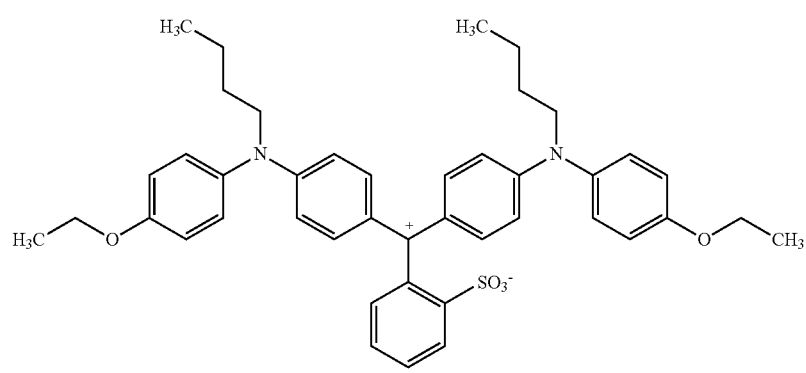
(A43)
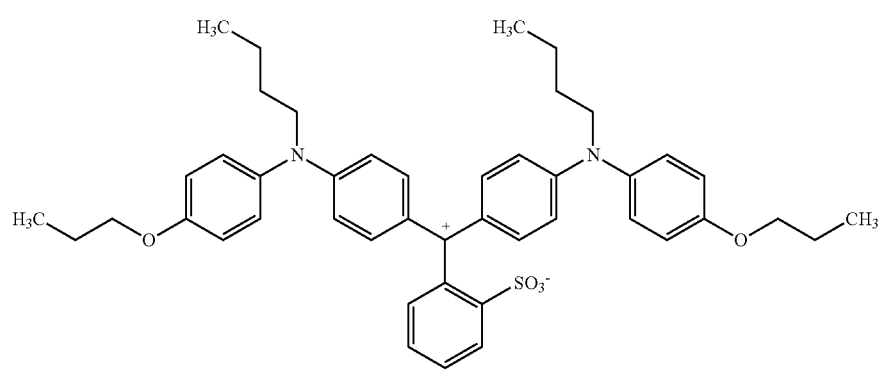
(A44)
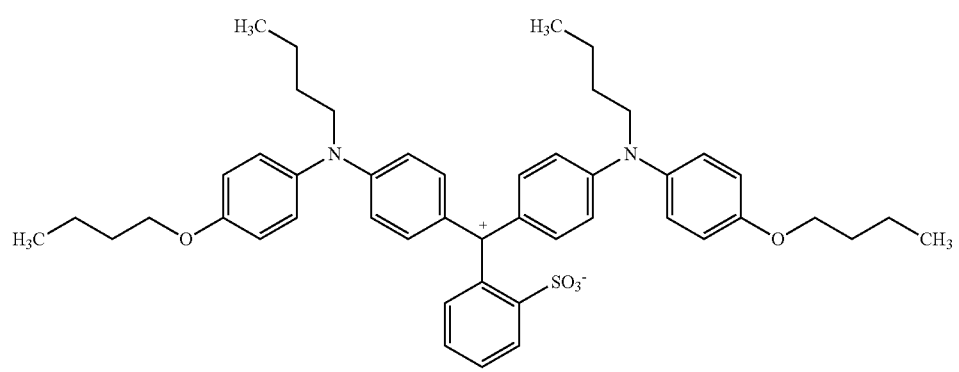
(A45)

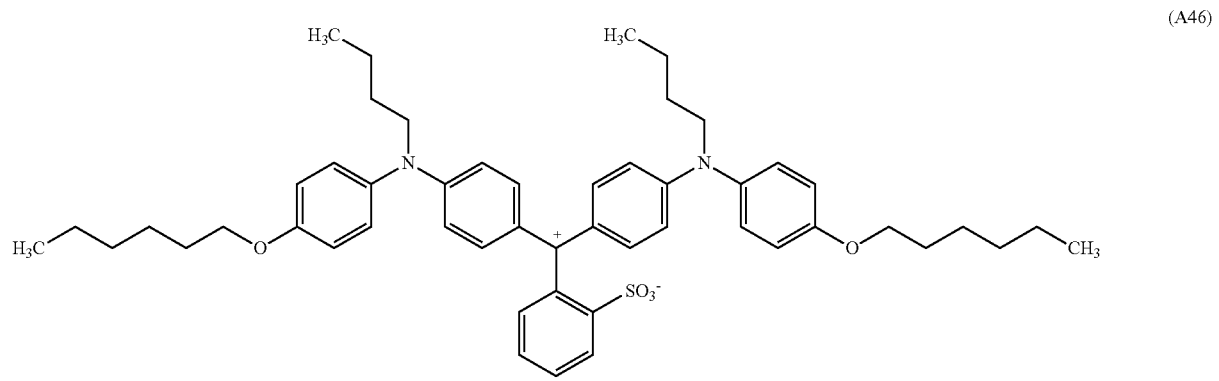
(A46)
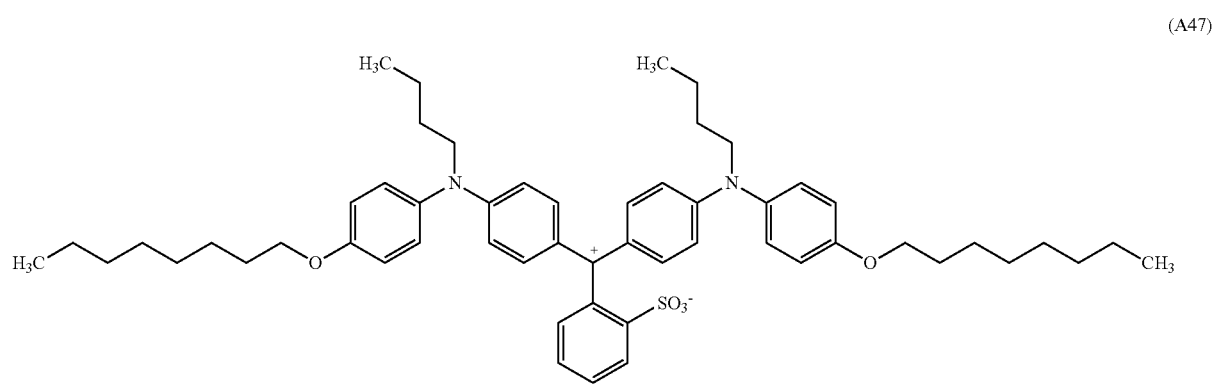
(A47)
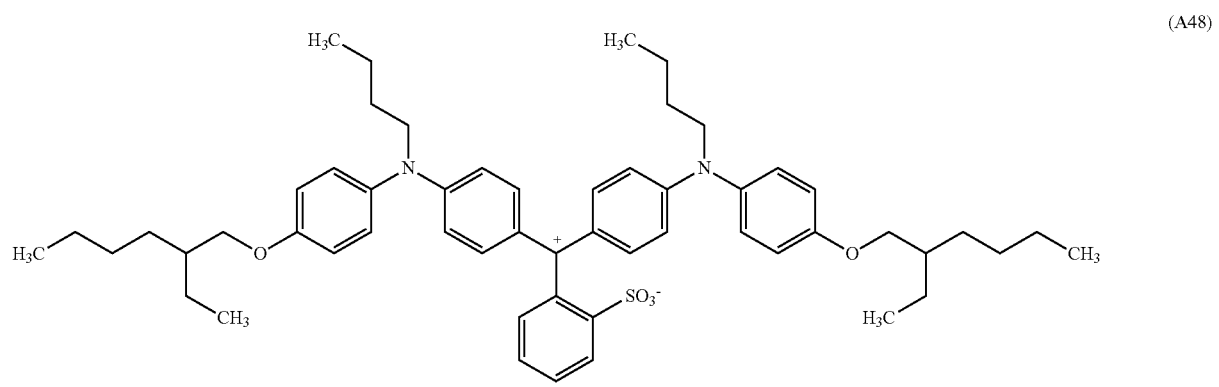
(A48)
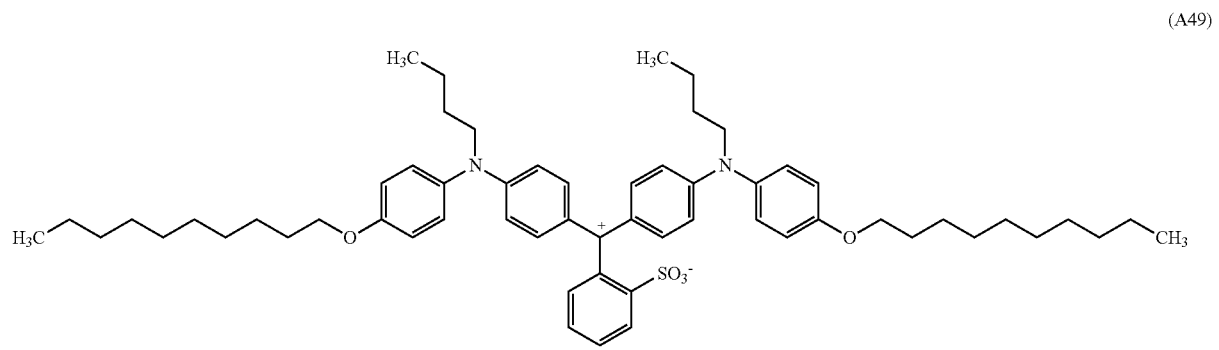
(A49)

(A50)
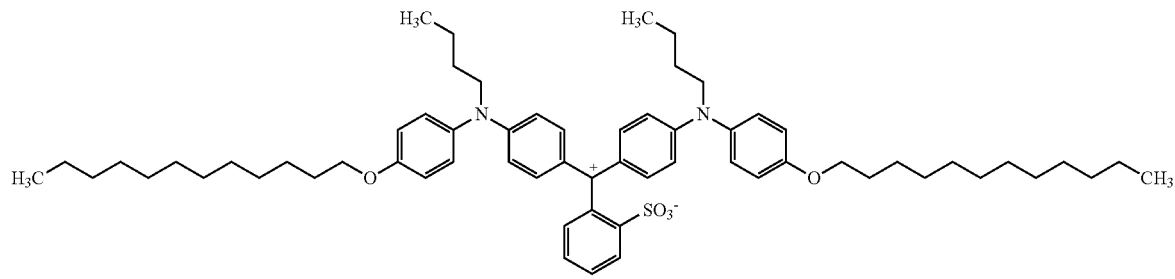
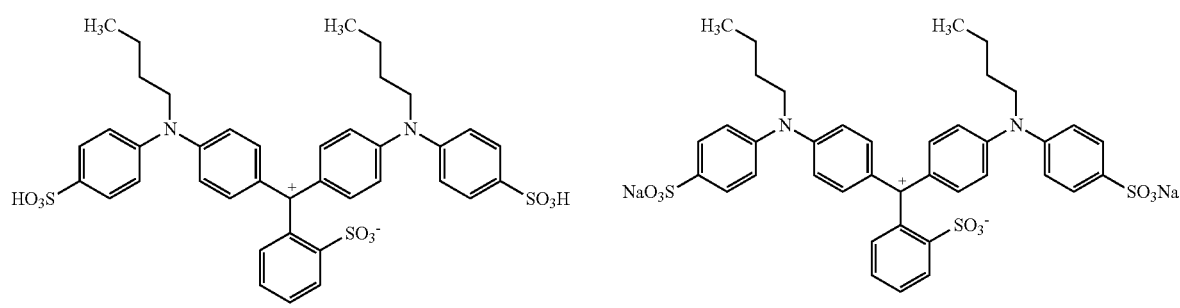
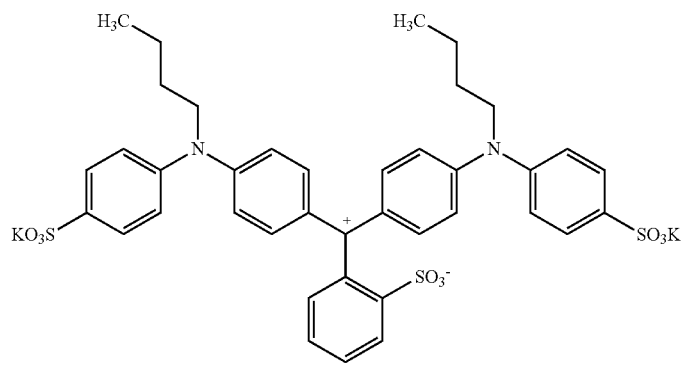
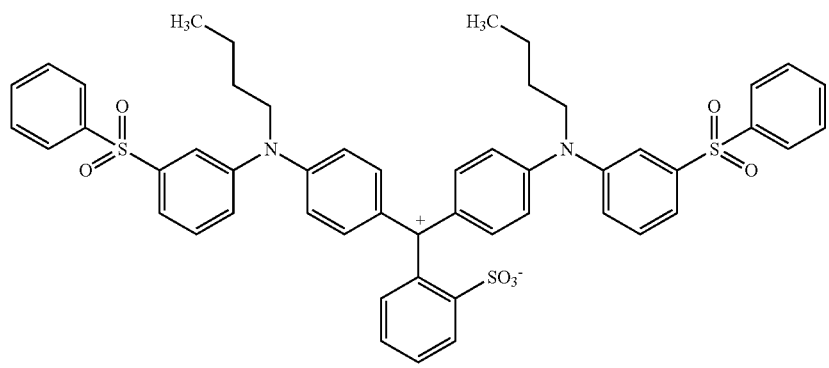

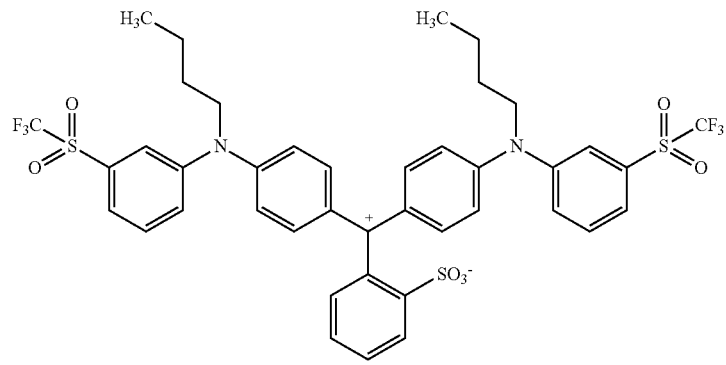
(A55)
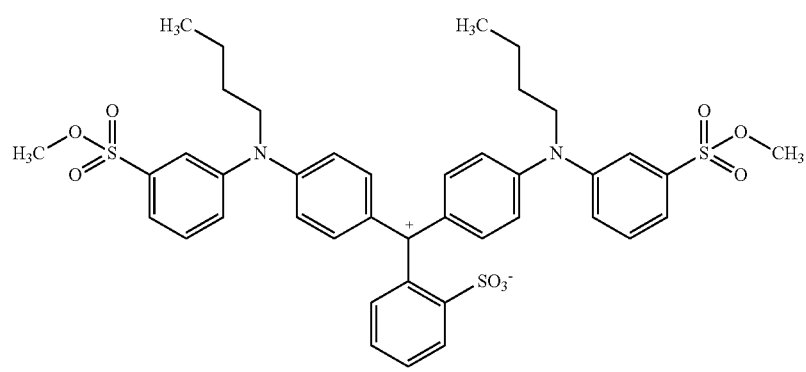
(A56)
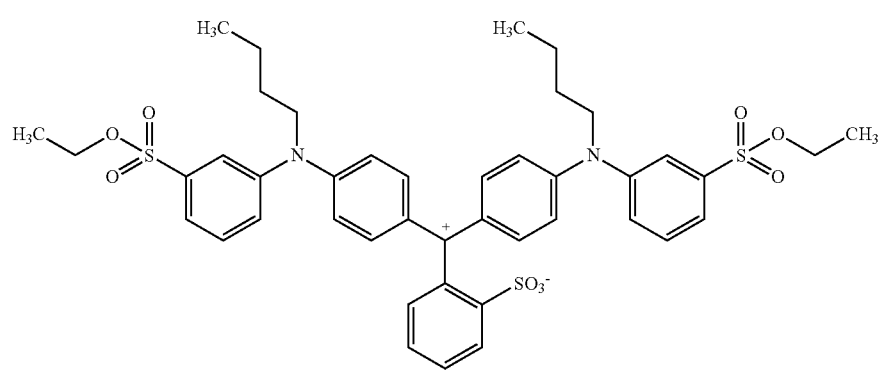
(A57)
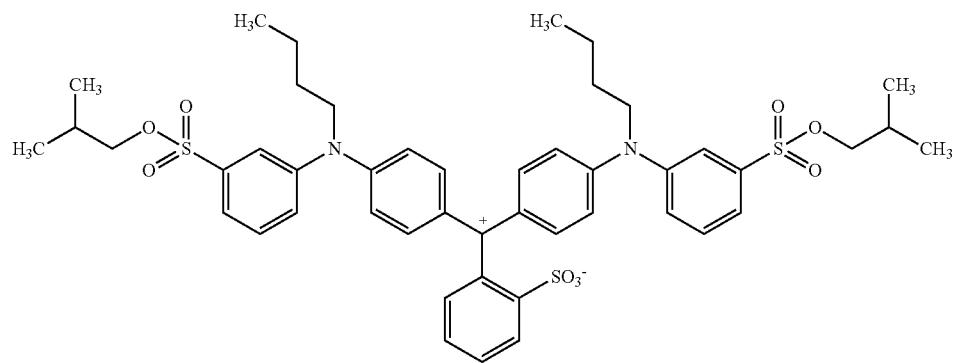
(A58)

-continued
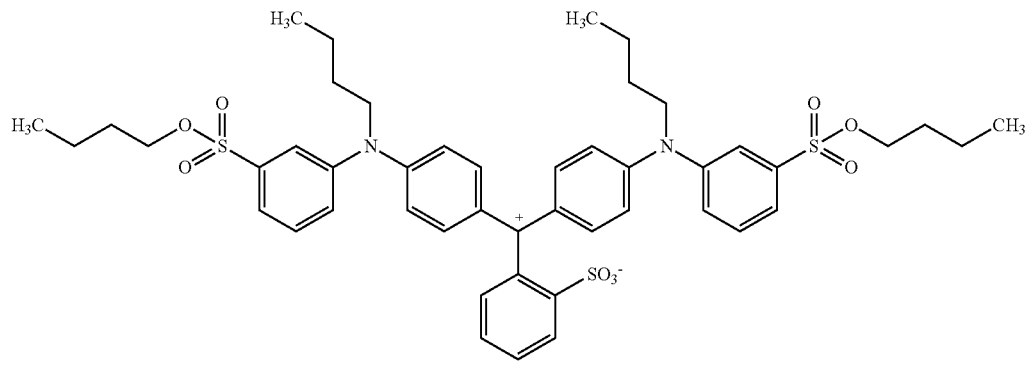
(A59)
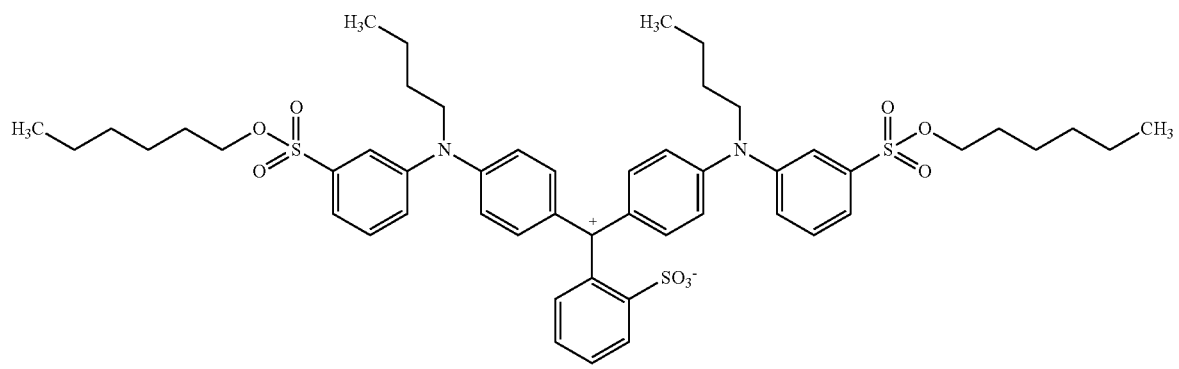
(A60)
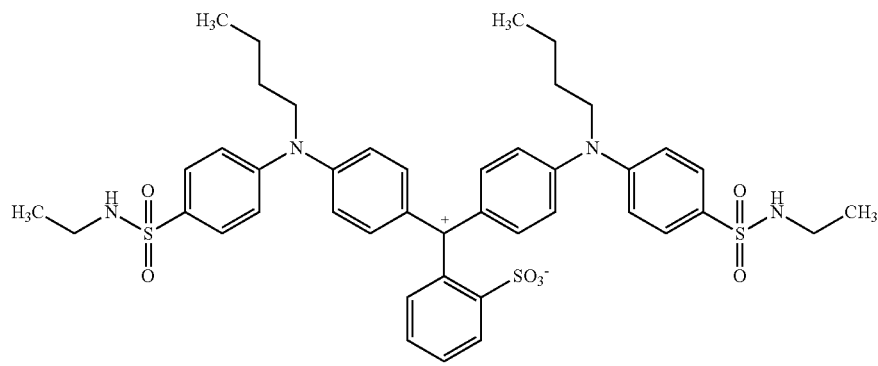
(A61)
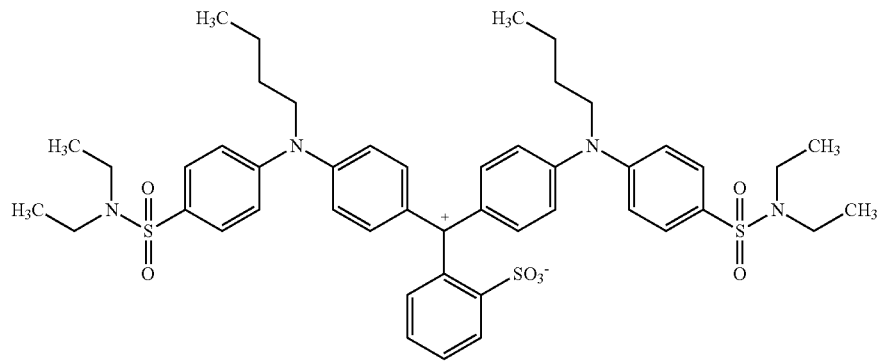
(A62)

-continued
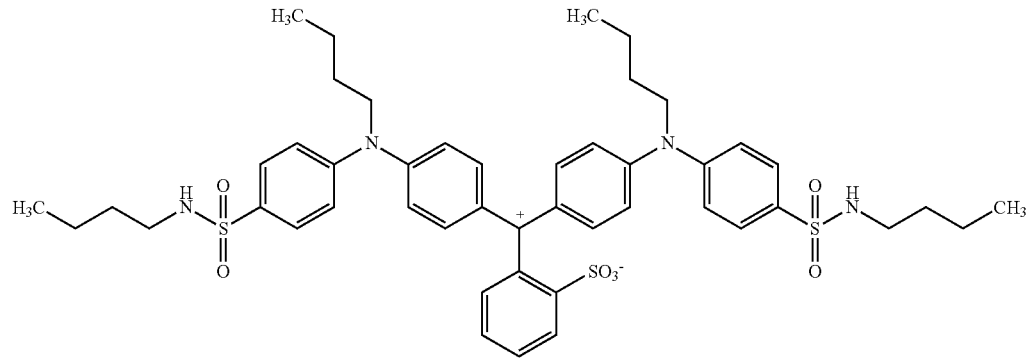
(A63)
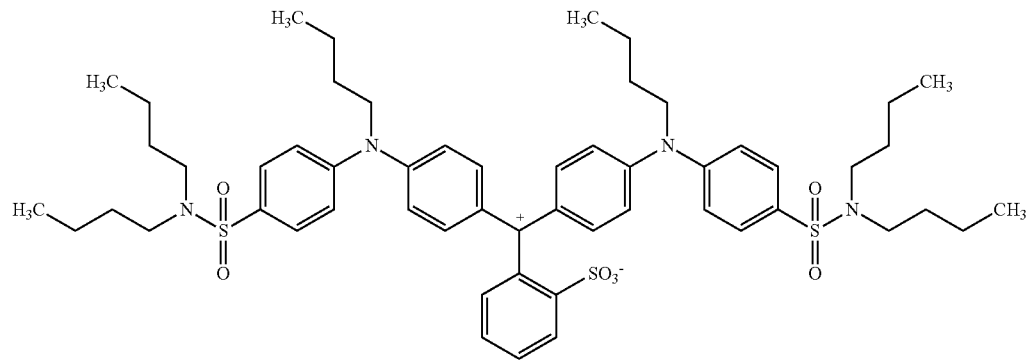
(A64)
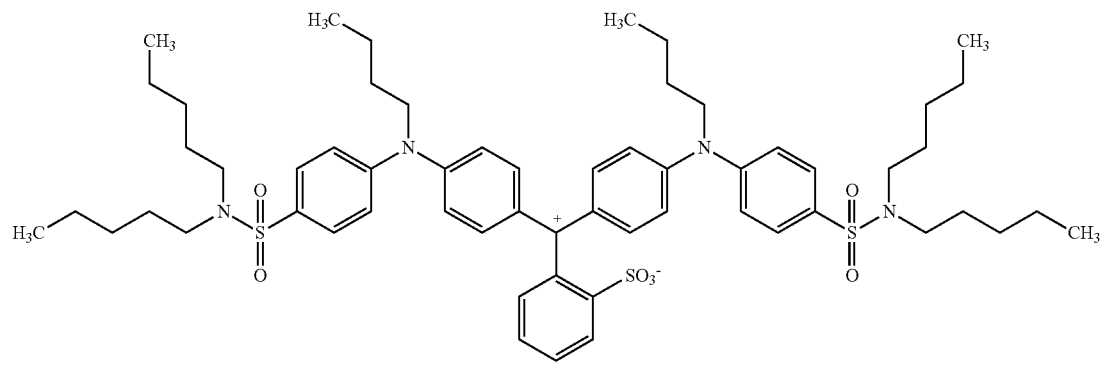
(A65)
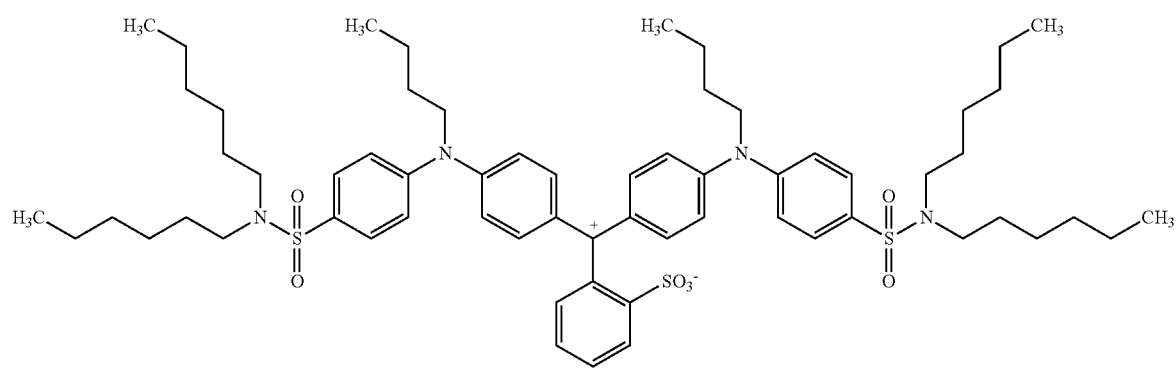
(A66)

-continued
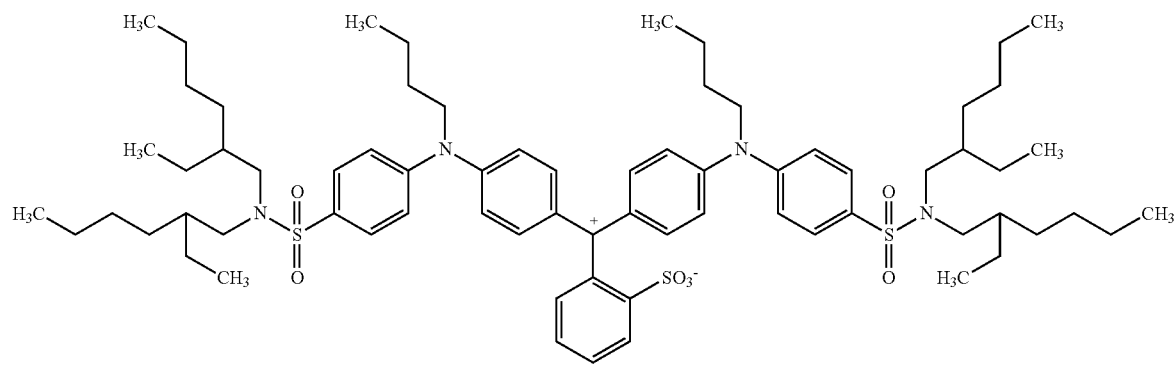
(A67)
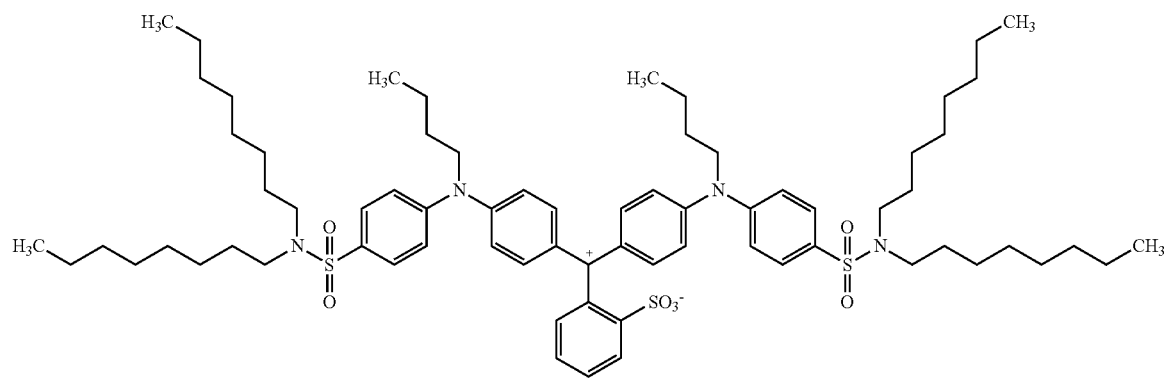
(A68)
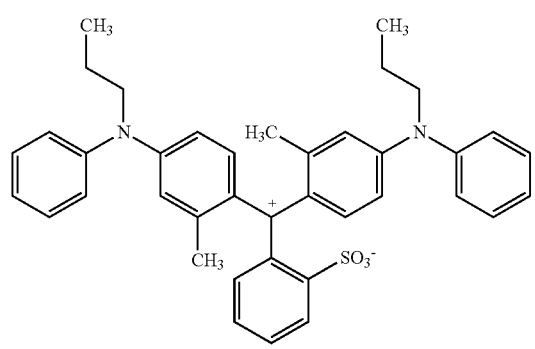
(A69)
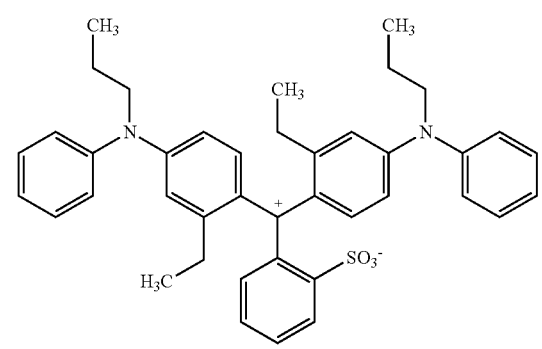
(A70)
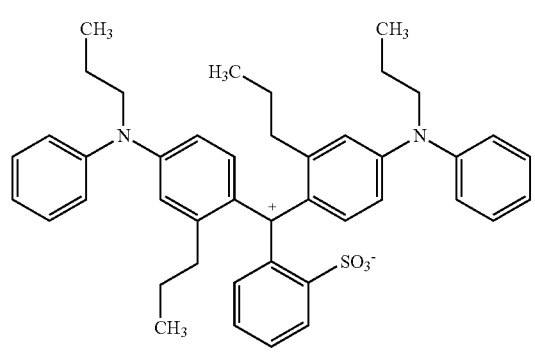
(A71)
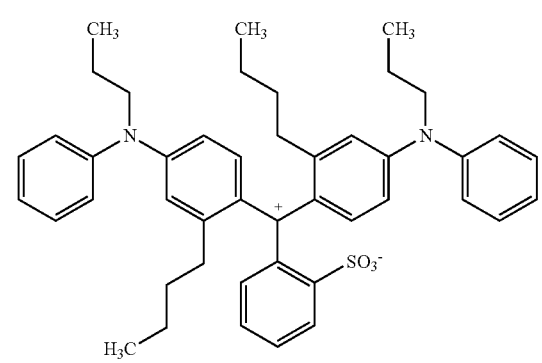
(A72)

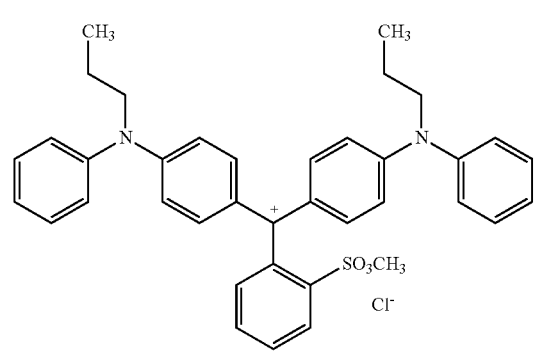
(A73)
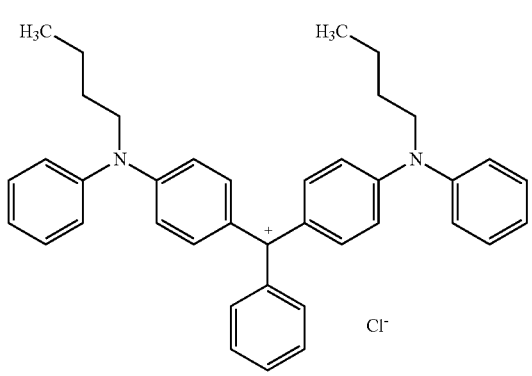
(A74)
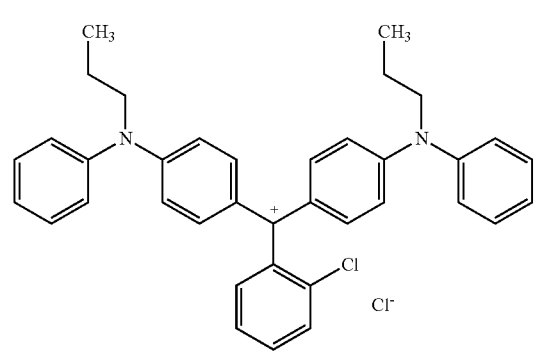
(A76)
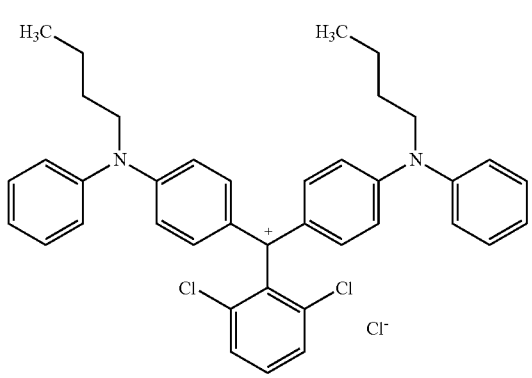
(A77)
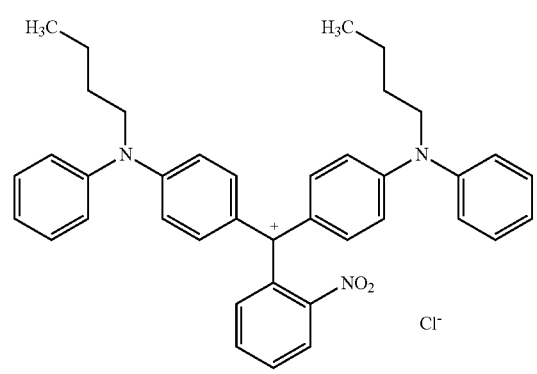
(A78)
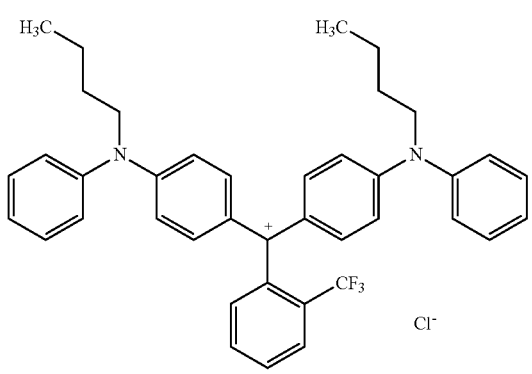
(A79)
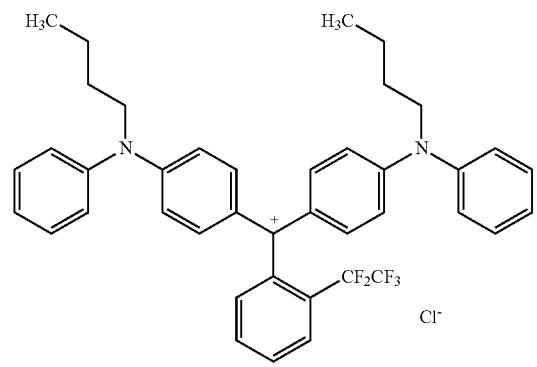
(A80)
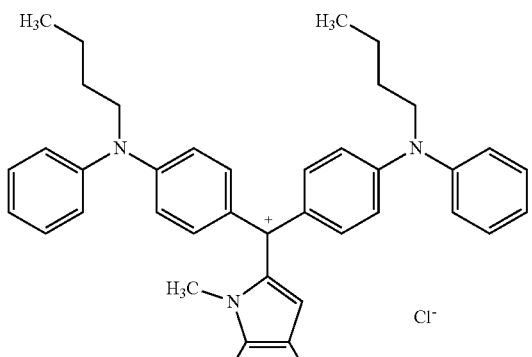
(A91)

-continued
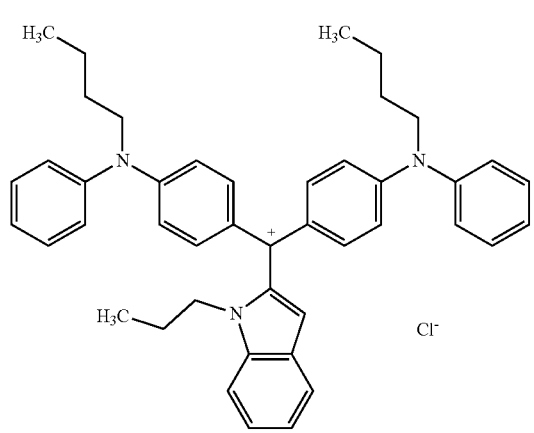
(A92)
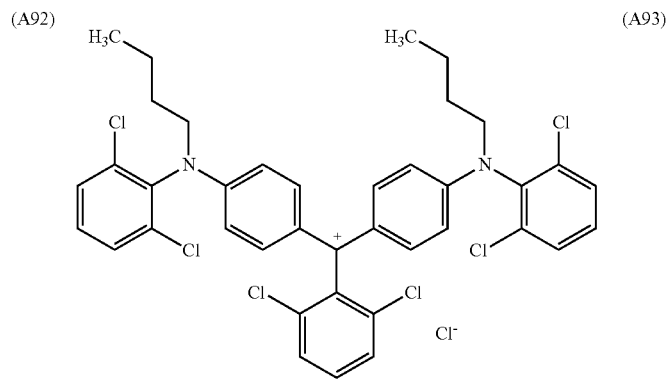
(A93)
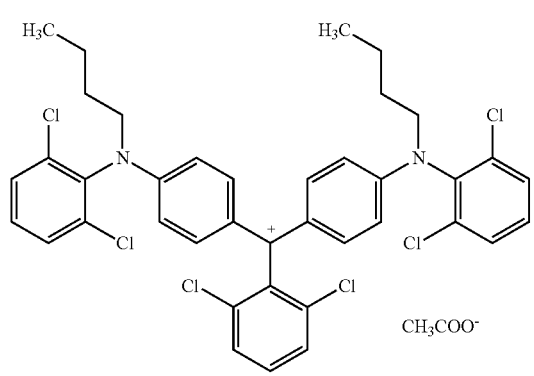
(A94)
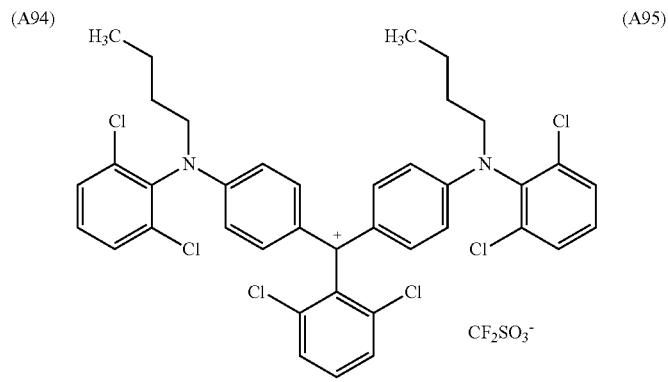
(A95)
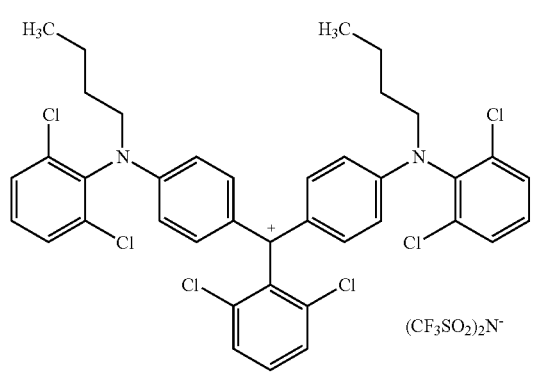
(A96)
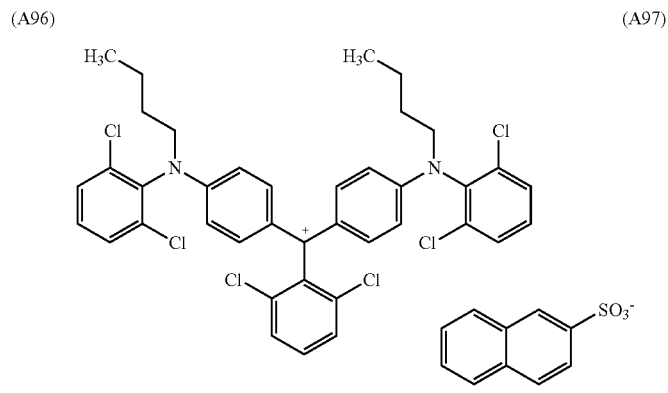
(A97)
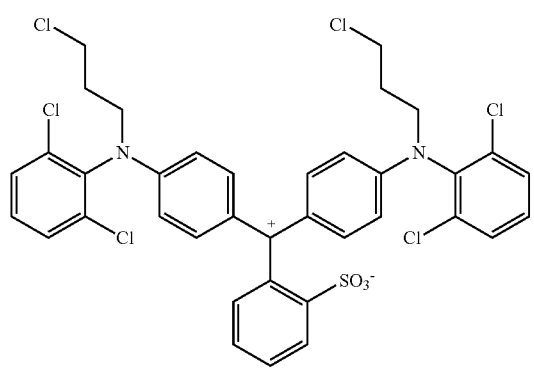
(A98)
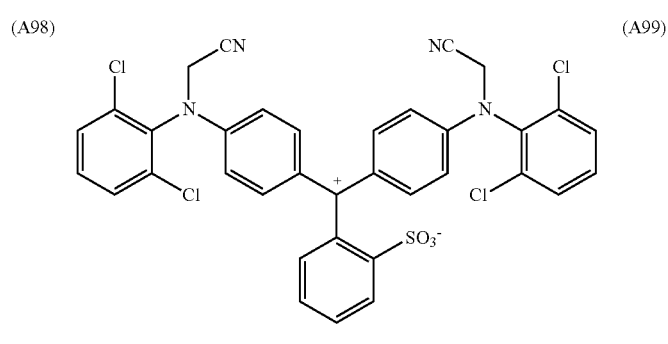
(A99)

-continued

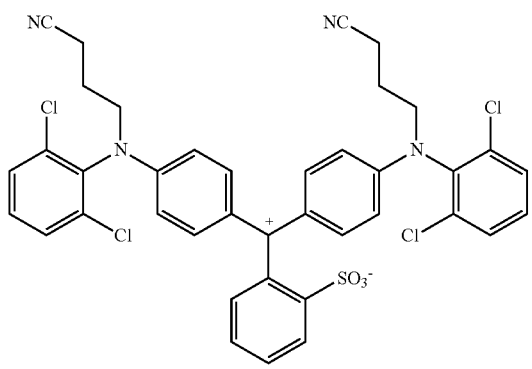
(A100)

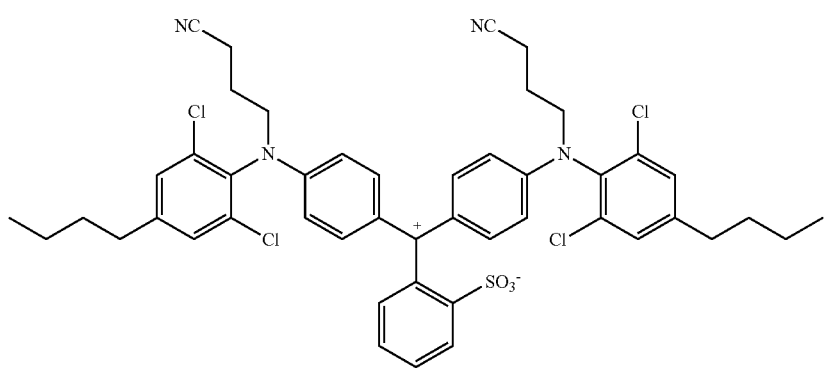
(A101)

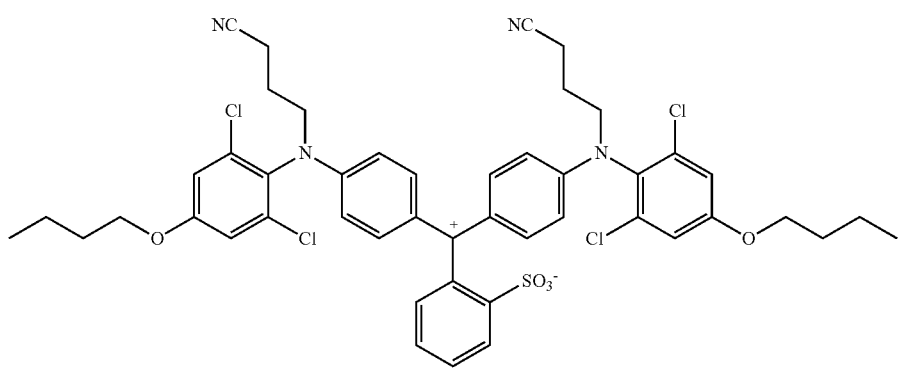
(A102)

Among them, in terms of excellent light fastness and storage stability, preferred compounds are as follows: compounds represented by compounds (A2), (A3), (A4), (A5), (A6), (A8), (A9), (A10), (A18), (A19), (A22), (A23), (A24), (A25), (A26), (A27), (A28), (A29), (A30), (A31), (A40), (A41), (A42), (A43), (A44), (A45), (A46), (A47), (A48), (A49), (A59), (A60), (A64), (A65), (A66), (A67), (A68), (A76), (A77), (A78), (A79), (A80), (A91), (A92), (A93), (A94), (A95), (A96), (A97), (A98), (A99), (A100), (A101), and (A102).

Among them, the compound (A2), (A4), (A5), (A6), (A8), (A18), (A19), (A24), (A25), (A26), (A27), (A28), (A40), (A45), (A46), (A64), (A65), (A98), (A100), (A101), or (A102) is more preferable, in terms of further excellent light fastness and storage stability.

In the compound represented by Formula (1), a cation may be delocalized, and the cation moiety may be present in any position in the molecule. Any case falls within the technical scope of the present invention. For example, in the case of the compound (A1) having an anionic substituent in the molecule, $X^-$ in Formula (1) is absent, and a structure thereof is changed as follows.

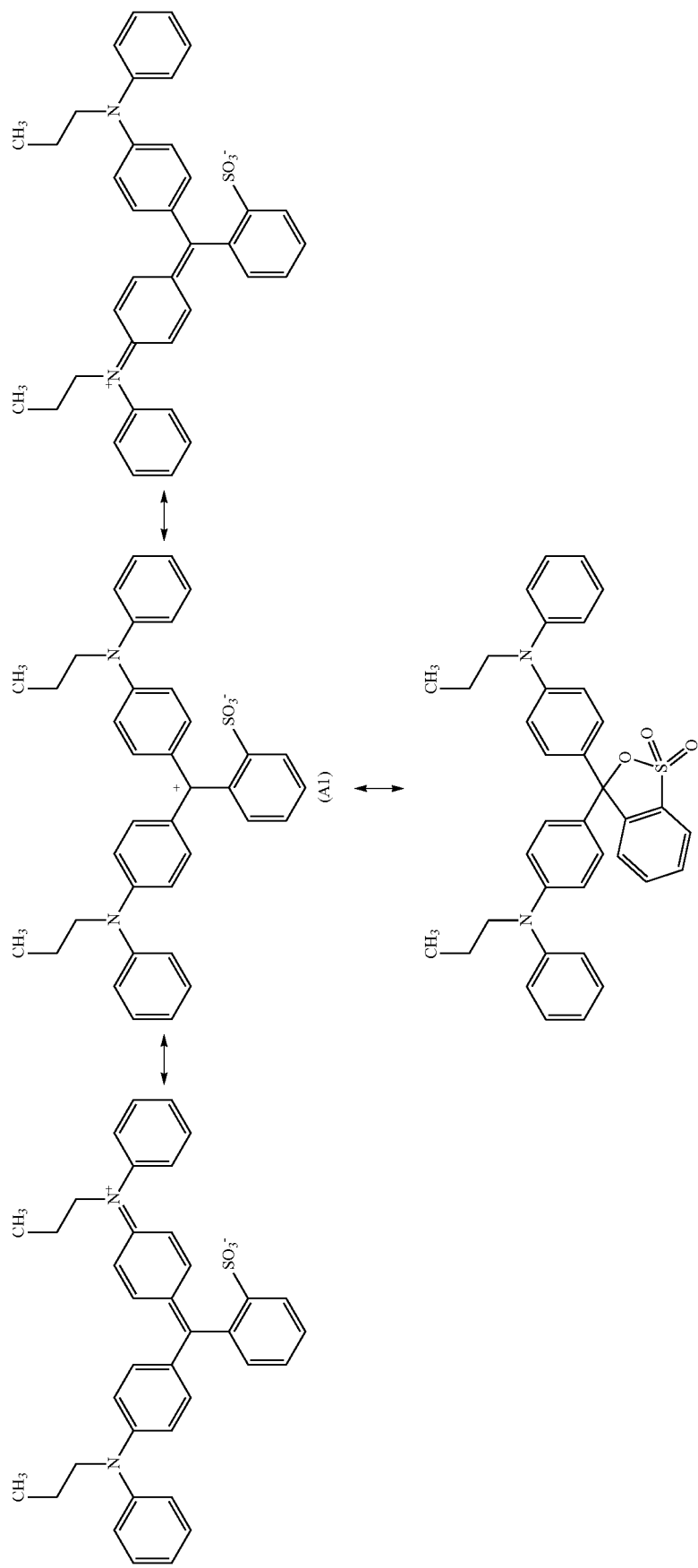

On the other hand, in the case of the compound (A74) having no anionic substituent in the molecule, a structure thereof is changed as follows.

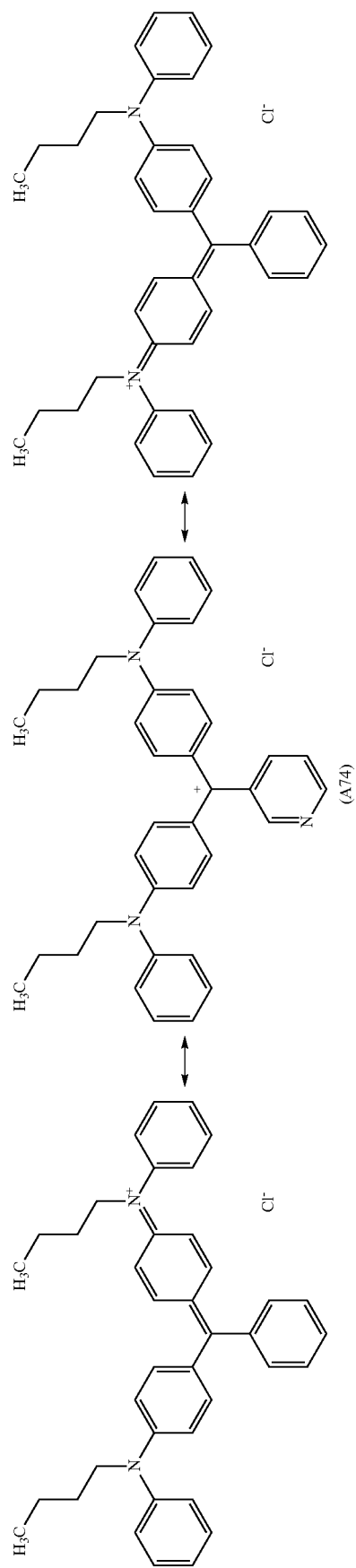
(A74)

The compound represented by Formula (1) can be synthesized based on a known method. That is, the compound represented by Formula (1) can be synthesized by a condensation step of condensing the following compounds (A), (B), and (C) to obtain a compound (D), and a subsequent oxidation step of oxidizing the compound (D). The condensation step and the oxidation step can be performed in the presence of a liquid medium, a condensing agent, or an oxidant, if necessary.

An example of a synthesis scheme is shown below, but is not limited to the present synthesis method. In the synthesis scheme, $R_1$ to $R_7$ in the compounds (A) to (D) are the same as $R_1$ to $R_7$ in Formula (1), respectively. The compound represented by Formula (1) can be synthesized as a mixture of a plurality of isomers that are different in kind, number, or position of substituents; however, for simplicity, the compound in the present invention is described as a "compound" even in a case where the compound is a mixture. Compounds used in the synthesis scheme are described as free-acid forms, but compounds in salt forms may also be used.

In a case of synthesizing a compound in which $R_1$ and $R_2$, $R_3$ and $R_4$, and $R_5$ and $R_6$ in Formula (1) are identical substituents, respectively, the same compounds may be used as the compounds (A) and (B).

[Synthesis Scheme 1]

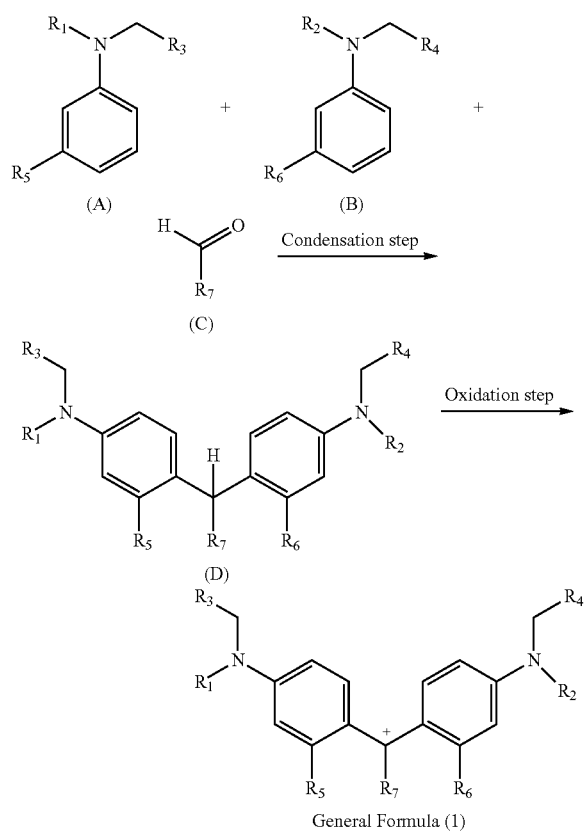

(Condensation Step)

First, the condensation step will be described. The condensation step can be performed in the presence of a medium, a condensing agent, or an oxidant, if necessary.

The condensation step can be performed without a solvent, but is preferably performed using a medium.

The medium that can be used in the condensation step is not particularly limited, but examples thereof can include the following materials, which may be used alone or as a mixture at an arbitrary mixing ratio, such as, water, methanol, ethanol, n-propanol, isopropanol, n-butanol, tert-butanol, ethylene glycol, glycerol, tetrahydrofuran, N,N-dimethylformamide, N,N-dimethylacetamide, N-methyl-2-pyrrolidone, 1,3-dimethyl-2-imidazolidinone, dimethyl sulfoxide, sulfolane, N,N'-dimethylpropyleneurea, chlorobenzene, 1,2-dichlorobenzene, nitrobenzene, and ethyl acetate.

Water, methanol, ethanol, or N,N-dimethylformamide is particularly preferable. The amount of the reaction solvent used is preferably 0.1 to 1000 mass %, and more preferably 1.0 to 150 mass %, with respect to an aldehyde compound (C).

The condensing agent that can be used in the condensation step is not particularly limited, but examples thereof can include sulfuric acid, hydrochloric acid, phosphoric acid, acetic acid, formic acid, aluminum chloride, zinc chloride, and p-toluenesulfonic acid. Sulfuric acid, hydrochloric acid, or acetic acid is particularly preferable. The amount of the condensing agent used is preferably 0.01 to 20 mass %, and more preferably 0.1 to 10 mass %, with respect to the aldehyde compound (C).

In addition, a reaction temperature in the condensation step can be in a range of 0 to 160° C. In particular, the reaction temperature is preferably 50° C. to 140° C., and more preferably 60° C. to 120° C. The present condensation reaction is generally terminated within 24 hours. After the termination of the reaction, column purification or purification by crystallization can be performed.

(Oxidation Step)

Next, the oxidation step will be described. The oxidation step can be performed in the presence of a medium or an oxidant, if necessary.

The oxidation step can be performed without a solvent, but is preferably performed using a medium.

The medium that can be used in the oxidation step is not particularly limited, but examples thereof can include the following materials, which may be used alone or as a mixture at an arbitrary mixing ratio, such as, water, methanol, ethanol, n-propanol, isopropanol, n-butanol, tert-butanol, ethylene glycol, glycerol, tetrahydrofuran, N,N-dimethylformamide, N,N-dimethylacetamide, N-methyl-2-pyrrolidone, 1,3-dimethyl-2-imidazolidinone, dimethyl sulfoxide, sulfolane, N,N'-dimethylpropyleneurea, chlorobenzene, 1,2-dichlorobenzene, nitrobenzene, ethyl acetate, and chloroform.

In particular, 1,2-dichlorobenzene, ethyl acetate, or chloroform is preferable. The amount of the reaction solvent used is preferably 0.1 to 1000 mass %, and more preferably 1.0 to 200 mass %, with respect to the aldehyde compound (C).

The oxidant that can be used in the oxidation step is not particularly limited, but examples thereof can include zinc oxide, iron oxide, manganese oxide, hydrogen peroxide, chloranil, or oxygen.

Manganese oxide or chloranil is preferable. The amount of the oxidant used is preferably 0.01 to 20 mass %, and more preferably 0.1 to 5 mass %, with respect to the aldehyde compound (C).

A pH of the medium in the oxidation step is preferably a pH of 1 to 9, more preferably a pH of 2 to 8, and particularly preferably a pH of 3 to 7.

A reaction temperature in the oxidation step can be in a range of 0 to 150° C. The reaction temperature is preferably 10° C. to 100° C., and particularly preferably 20° C. to 80° C. The present oxidation reaction is generally terminated within 18 hours. After the termination of the reaction, column purification or purification by crystallization can be performed.

The compounds represented by Formula (1) may be used alone, or, if necessary, in combination of two or more thereof in order to adjust a tone and the like. Furthermore, the compound can be used in combination with a known pigment or dye. Two or more known pigments or dyes may be used in combination.

Hereinafter, an ink, a resist composition for a color filter, a sheet for heat-sensitive transfer recording, and a toner that are obtained by using the compound represented by Formula (1) will be described in this order.

<Ink>

First, the ink according to the present invention will be described. The compound represented by Formula (1) has excellent light fastness and storage stability. Therefore, the compound is suitable as a coloring agent of the ink. The ink of the present invention contains a medium and the compound represented by Formula (1) as a coloring agent. The compound is present in a dissolved or dispersed state in the medium. In the ink of the present invention, a constituent component other than the compound represented by Formula (1) is adequately selected depending on an application of the ink. In addition, in a range in which characteristics for various applications are not degraded, an additive and the like may be adequately added.

The ink of the present invention is preferably used as an ink for a transfer sheet for a heat-sensitive transfer recording type printer, printing ink, paint, writing ink, and textile printing ink.

When the ink of the present invention is used as a textile printing ink, fabric on which textile printing can be performed is not particularly limited as long as it can be dyed, but examples thereof can include fabric made of fibers containing polyester, acetate, and triacetate. The fabric may be in any form such as woven fabric, knitted fabric, or non-woven fabric. In addition, fabric made of cotton, silk, hemp, polyurethane, acryl, nylon, wool, or rayon fiber, or blended fabric of two or more of these fibers can be used.

A thickness of a yarn forming the fabric is preferably in a range of 10 to 100 denier. In addition, a thickness of a fiber forming the yarn is not particularly limited, but is preferably 1 denier or less.

The ink of the present invention can be prepared as follows.

The compound of the present invention is gradually added to the medium together with another coloring agent, an emulsifier, a resin, and the like, if necessary, while performing stirring to be sufficiently mixed with the medium. Furthermore, the ink of the present invention can be obtained by applying a mechanical shearing force and performing stable dissolution or fine dispersion with a disperser.

[Medium]

In the present invention, the "medium" refers to water or an organic solvent. In a case where an organic solvent is used as the medium, the kind of organic solvent is selected depending on a purpose or an application of the ink and is not particularly limited. Examples of the organic solvent can include the following: alcohols such as methanol, ethanol, modified ethanol, isopropanol, n-butanol, isobutanol, tert-butanol, sec-butanol, 2-methyl-2-butanol, 3-pentanol, octanol, benzyl alcohol, and cyclohexanol; glycols such as methyl cellosolve, ethyl cellosolve, diethylene glycol, and diethylene glycol monobutyl ether; ketones such as acetone, methyl ethyl ketone, and methyl isobutyl ketone; esters such as ethyl acetate, butyl acetate, ethyl propionate, and cellosolve acetate; aliphatic hydrocarbons such as hexane, octane, petroleum ether, and cyclohexane; aromatic hydrocarbons such as benzene, toluene, and xylene; halogenated hydrocarbons such as carbon tetrachloride, trichloroethylene, and tetrabromoethane; ethers such as diethyl ether, dimethyl glycol, trioxane, and tetrahydrofuran; acetals such as methylal and diethyl acetal; organic acids such as formic acid, acetic acid, and propionic acid; and sulfur or nitrogen-containing organic compounds such as nitrobenzene, dimethylamine, monoethanolamine, pyridine, dimethyl sulfoxide, and dimethylformamide.

In addition, as the organic solvent, a polymerizable monomer can be used. Examples of the polymerizable monomer can include an addition polymerizable monomer and a condensation monomer, and an addition polymerizable monomer is preferable. Specific examples of the polymerizable monomer can include the following: a styrene-based monomer such as styrene, α-methylstyrene, α-ethylstyrene, o-methylstyrene, m-methylstyrene, p-methylstyrene, o-ethylstyrene, m-ethylstyrene, or p-ethylstyrene; an acrylate-based monomer such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, or amide acrylate; a methacrylate-based monomer such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, or amide methacrylate; an olefin-based monomer such as ethylene, propylene, butylene, butadiene, isoprene, isobutylene, or cyclohexane; a halogenated vinyl-based monomer such as vinyl chloride, vinylidene chloride, vinyl bromide, or vinyl iodide; a vinyl ester-based monomer such as vinyl acetate, vinyl propionate, or vinyl benzoic acid; a vinyl ether-based monomer such as vinyl methyl ether, vinyl ethyl ether, or vinyl isobutyl ether; and a vinyl ketone-based monomer such as vinyl methyl ketone, vinyl hexyl ketone, or methyl isopropenyl ketone. These polymerizable monomers may be used alone, or, if necessary, in combination of two or more thereof.

[Dispersant]

In a case where water is used as the medium of the ink according to the present invention, in order to obtain excellent storage stability of the coloring agent, a dispersant may be added, if necessary. The dispersant is not particularly limited, but examples thereof can include a cationic surfactant, an anionic surfactant, and a nonionic surfactant.

Examples of the cationic surfactant can include the following: dodecylammonium chloride, dodecylammonium bromide, dodecyltrimethylammonium bromide, dodecylpyridinium chloride, dodecylpyridinium bromide, and hexadecyltrimethylammonium bromide.

Examples of the anionic surfactant can include the following: a fatty acid soap such as sodium stearate or sodium dodecanoate, sodium dodecyl sulfate, sodium dodecylbenzene sulfate, sodium lauryl sulfate, naphthalene, and a formalin condensate of β-naphthalene sulfonic acid.

Examples of the nonionic surfactant can include the following: dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

[Coloring Agent]

In the coloring agent constituting the ink of the present invention, although the compound represented by Formula (1) is used, the compounds may be used alone or in combination of two or more thereof. In addition, within a range in which solubility or dispersibility of the compound in the medium is not inhibited, another coloring agent such as a known dye may also be used together. The other coloring agent that can be used together is not particularly limited, but examples thereof can include a condensed azo compound, an azo metal complex, and a methine compound.

A content of the coloring agent is preferably 1.0 to 30 parts by mass, more preferably 2.0 to 20 parts by mass, and particularly preferably 3.0 to 15 parts by mass, with respect to 100 parts by mass of the medium. Within the above range, sufficient coloring power can be obtained and dispersibility of the coloring agent is excellent.

[Resin]

The ink of the present invention may further contain a resin. The kind of resin is determined depending on the purpose or the application of the ink, but is not particularly limited. Examples thereof can include the following: a styrene-based polymer, an acrylic acid-based polymer, a methacrylic acid-based polymer, a polyester resin, a polyvinyl ether resin, a polyvinyl methyl ether resin, a polyvinyl alcohol resin, a polyvinyl butyral resin, a polyurethane resin, and a polypeptide resin. These resins may be used alone, or, if necessary, in combination of two or more thereof.

The disperser is not particularly limited, but a media type disperser such as a rotating shear type homogenizer, a ball mill, a sand mill, or an attritor, or a high-pressure counter collision type disperser can be used.

As described above, since the ink of the present invention contains the compound represented by Formula (1), it is possible to provide an ink having high light fastness and excellent storage stability.

<Sheet for Heat-Sensitive Transfer Recording>

Next, the sheet for heat-sensitive transfer recording according to the present invention will be described. Since the compound of the present invention has high light fastness and excellent storage stability, the compound can be preferably used for the sheet for heat-sensitive transfer recording.

The sheet for heat-sensitive transfer recording according to the present invention includes a substrate and a coloring material layer formed on the substrate in a film form by using a composition containing the compound of the present invention. The coloring material layer has at least a yellow layer, a magenta layer, and a cyan layer.

In a heat-sensitive transfer recording method, in a state in which the coloring material layer of the sheet for heat-sensitive transfer recording is overlapped with an image receiving sheet having a surface on which a coloring material receiving layer is provided, the sheet for heat-sensitive transfer recording is heated using a heating unit such as a thermal head. By doing so, the coloring material in the sheet for heat-sensitive transfer recording is transferred onto the image receiving sheet, thereby forming an image.

Specifically, the cyan layer in the coloring material layer is formed by applying the ink of the present invention described above to a substrate sheet and drying the ink. Hereinafter, more details will be described.

A coloring material containing the compound represented by Formula (1), a binder resin, and if necessary, a surfactant and a wax are gradually added to the medium while performing stirring to be sufficiently mixed with the medium. Subsequently, the composition is stably dissolved or dispersed into a fine particle shape by applying a mechanical shearing force with a disperser, thereby preparing an ink. The ink is applied to a base film, which is a substrate, and then dried to form a coloring material layer. Furthermore, if necessary, a transfer protective layer and a heat resistant lubricant layer to be described below are formed, thereby obtaining the sheet for heat-sensitive transfer recording of the present invention. The sheet for heat-sensitive transfer recording of the present invention is not limited to a sheet for heat-sensitive transfer recording prepared by the above production method. Hereinafter, respective components used in the coloring material layer will be described in detail.

[Coloring Material]

In the coloring material, although the compound represented by Formula (1) is used, the compounds may be used alone or in combination of two or more thereof. In addition, a coloring material used in the related art for thermal transfer can be used together. For the coloring material to be used together, a hue, printing sensitivity, light fastness, preservability, and solubility in the binder resin are required to be taken into consideration. The amount of the coloring material used is 1 to 150 parts by mass, with respect to 100 parts by mass of the binder resin contained in the coloring material layer. The amount of the coloring material used is preferably 50 to 120 parts by mass, from the viewpoint of dispersibility of the coloring material in a dispersion liquid. When two or more coloring materials are mixed, a total mass thereof is preferably in the above range.

[Binder Resin]

The binder resin is not particularly limited, but it is preferable to use the following resins: a water-soluble resin such as a cellulose resin, a polyacrylic acid resin, a starch resin, or an epoxy resin; and an organic solvent soluble resin such as a polyacrylate resin, a polymethacrylate resin, a polystyrene resin, a polycarbonate resin, a polyether sulfone resin, a polyvinyl butyral resin, an ethyl cellulose resin, an acetyl cellulose resin, a polyester resin, an AS resin, or a phenoxy resin. These resins may be used alone, or, if necessary, in combination of two or more thereof.

[Surfactant]

In order to impart sufficient lubricity to the sheet for heat-sensitive transfer recording of the present invention during heating of the thermal head (during printing), a surfactant may be added.

[Wax]

In order to impart sufficient lubricity to the sheet for heat-sensitive transfer recording of the present invention during non-heating of the thermal head, a wax may be added. Examples of the wax that can be added can include a polyethylene wax, a paraffin wax, and a fatty acid ester wax, but are not limited thereto.

In addition to the above additives, if necessary, an ultraviolet absorber, an antiseptic agent, an antioxidant, an antistatic agent, a viscosity modifier, and the like may be added to the sheet for heat-sensitive transfer recording of the present invention.

[Medium]

When the coloring material layer is formed, the medium used for preparing a dispersion is not particularly limited, but examples thereof can include water and an organic solvent. Examples of the organic solvent can include the following: alcohols such as methanol, ethanol, isopropanol, and isobutanol; cellosolves such as methyl cellosolve and ethyl cellosolve; aromatic hydrocarbons such as toluene, xylene, and chlorobenzene; esters such as ethyl acetate and butyl acetate; ketones such as acetone, methyl ethyl ketone, methyl isobutyl ketone, and cyclohexanone; halogenated hydrocarbons such as methylene chloride, chloroform, and trichloroethylene; ethers such as tetrahydrofuran and dioxane; and N,N-dimethylformamide, and N-methyl pyrrolidone. These organic solvents may be used alone, or, if necessary, in combination of two or more thereof.

[Substrate]

Next, the substrate constituting the sheet for heat-sensitive transfer recording will be described. Any substrate may be used without particular limitation as long as it is a film that supports the coloring material layer and has a heat resistance and a strength to some extent, and a known substrate can be used. Examples thereof can include the following: a polyethylene terephthalate film, a polyethylene naphthalate film, a polycarbonate film, a polyimide film, a polyamide film, an aramid film, a polystyrene film, a 1,4-polycyclohexylenedimethylene terephthalate film, a polysulfone film, a polypropylene film, a polyphenylene sulfide film, a polyvinyl alcohol film, cellophane, a cellulose derivative, a polyethylene film, a polyvinyl chloride film, a nylon film, capacitor paper, and paraffin paper. Among them, a polyethylene terephthalate film is preferable from the viewpoints of a mechanical strength, solvent resistance, and economic efficiency.

A thickness of the substrate is 0.5 to 50 µm, and preferably 3 to 10 µm, from the viewpoint of transferability.

In a case where a dye ink is applied on the substrate to form the coloring material layer, wettability and adhesiveness of a coating liquid are likely to be insufficient. Therefore, it is preferable that a surface (forming surface) of the substrate on which the coloring material layer is formed is subjected to an adhesion treatment, if necessary. The forming surface of the coloring material layer may be formed on one side or both sides of the substrate. The adhesion treatment is not particularly limited, but examples thereof can include an ozone treatment, a corona discharge treatment, an ultraviolet treatment, a plasma treatment, a low-temperature plasma treatment, a primer treatment, and a chemical reagent treatment. In addition, these treatments may be performed in combination.

The adhesion treatment of the substrate may be performed by coating an adhesive layer on the substrate. The adhesive layer is not particularly limited, but examples thereof can include the following: a fine particle formed of an organic material such as a polyester resin, a polystyrene resin, a polyacrylic acid ester resin, a polyamide resin, a polyether resin, a polyvinyl acetate resin, a polyethylene resin, a polypropylene resin, a polyvinyl chloride resin, a polyvinyl alcohol resin, or a polyvinyl butyral resin, and a fine particle formed of an inorganic material such as silica, alumina, magnesium carbonate, magnesium oxide, or titanium oxide.

Since the sheet for heat-sensitive transfer recording of the present invention contains the compound represented by Formula (1), it is possible to provide a sheet for heat-sensitive transfer recording having high light fastness and excellent storage stability.

<Resist Composition for Color Filter and Color Filter>

Next, the resist composition for a color filter according to the present invention (hereinafter, also referred to as a "resist composition of the present invention") will be described. The compound represented by Formula (1) has high light fastness and excellent storage stability. Therefore, the compound is preferably used to adjust a color tone of the resist composition for a color filter. In addition, by using the resist composition of the present invention, a color filter having high light fastness and excellent storage stability can be obtained.

The resist composition for a color filter of the present invention contains a binder resin, a medium, and the compound of the present invention as a coloring agent. The resist composition for a color filter of the present invention can be obtained as described below. The compound of the present invention and the binder resin are added to the medium while being stirred. In this case, if necessary, a polymerizable monomer, a polymerization initiator, a photoacid generator, and the like may be added. Thereafter, the material is stably dissolved or finely dispersed in the medium by applying a mechanical shearing force with a disperser, thereby obtaining the resist composition for a color filter of the present invention.

[Binder Resin]

As a binder resin that can be used in the resist composition of the present invention, any binder resin may be used as long as any one of a light irradiation portion and a light shielding portion can be dissolved by an organic solvent, an alkali aqueous solution, water, or a commercially available developer in an exposure process of pixel formation. Among them, a binder resin having a composition that can be developed by water or an alkali aqueous solution is preferable from the viewpoints of workability and easiness in a treatment after resist preparation.

As the binder resin, a binder resin obtained by copolymerizing the following hydrophilic polymerizable monomer and the following lipophilic polymerizable monomer by a known method at an appropriate mixing ratio can be used.

Hydrophilic polymerizable monomer: acrylic acid, methacrylic acid, N-(2-hydroxyethyl)acrylamide, N-vinyl pyrrolidone, or a polymerizable monomer having an ammonium salt Lipophilic polymerizable monomer: acrylic acid ester, methacrylic acid ester, vinyl acetate, styrene, or N-vinyl carbazole These binder resins are used in combination with a radical polymerizable monomer having an ethylenic unsaturated group, a cationic polymerizable monomer having an oxirane ring or an oxetane ring group, a radical generator, an acid generator, and a base generator. This kind of binder resin can be used as a negative-type resist composition in which only a light shielding portion is removed by development in order to reduce solubility of a material at an exposure portion to the developer by exposure.

In addition, a resin having a quinone diazide group which is cleaved by light to generate a carboxylic acid can be used. Furthermore, a resin having a group which is cleaved by an acid, such as a tert-butyl carbonate ester of polyhydroxystyrene or tetrahydropyranyl ether, and an acid generator which generates an acid by exposure can be used in combination. This kind of resin can be used as a positive-type resist composition in which only an exposure portion is removed by development in order to improve solubility of a material at an exposure portion in the developer by exposure.

In a case where the resist composition of the present invention is the negative-type resist composition, a polymerizable monomer which performs addition polymerization by exposure (hereinafter, also referred to as a "photopolymerizable monomer") is preferably used as the binder resin. As the photopolymerizable monomer, it is preferable to use a compound having at least one addition-polymerizable ethylenic unsaturated double bond in a molecule and having a boiling point of 100° C. or higher at a normal pressure. Specifically, examples thereof can include the following: monofunctional acrylates and methacrylates such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; polyfunctional acrylates and methacrylates such as polyethylene glycol diacrylate, polyethylene glycol dimethacrylate, polypropylene glycol diacrylate, polypropylene glycol dimethacrylate, trimethylolethane triacrylate, trimethylolethane trimethacrylate, trimethylolpropane triacrylate, trimethylolpropane trimethacrylate, trimethylolpropane diacrylate, trimethylolpropane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylolpropane tri(acryloyloxy propyl)ether, tri(acryloyloxy ethyl)isocyanurate, tri(acryloyloxy ethyl)cyanurate, glycerol triacrylate, and glycerol trimethacrylate; and polyfunctional acrylates and polyfunctional methacrylates that can be obtained by adding ethylene oxide or propylene oxide to a polyfunctional alcohol such as trimethylol propane or glycerol, and then performing acrylation or methacrylation. Furthermore, it is possible to use urethane acrylates, polyester acrylates, or polyfunctional epoxy acrylates or epoxy methacrylates which are reaction products of an epoxy resin and acrylic acid or methacrylic acid.

Among the above photopolymerizable monomers, it is preferable to use the following monomers: trimethylolpropane triacrylate, trimethylolpropane trimethacrylate, pentaerythritol tetraacrylate, pentaerythritol tetramethacrylate, dipentaerythritol hexaacrylate, dipentaerythritol hexamethacrylate, dipentaerythritol pentaacrylate, and dipentaerythritol pentamethacrylate. The photopolymerizable monomers may be used alone, or, if necessary, in combination of two or more thereof.

A content of the photopolymerizable monomer is preferably 5 to 50 mass %, and more preferably 10 to 40 mass %, with respect to a mass (total solid content) of the resist composition according to the present invention. When the content is 5 to 50 mass %, the sensitivity to exposure can be further improved, and adhesion of the resist composition is also improved.

In a case where the resist composition of the present invention is the negative-type resist composition, a photopolymerization initiator may also be added. Examples of the photopolymerization initiator can include a vicinal polyketo aldol compound, an α-carbonyl compound, an acyloin ether, a multi-branched quinone compound, a combination of a triallyl imidazole dimer and p-aminophenyl ketone, and a tri-oxadiazole compound. Among them, 2-benzyl-2-dimethylamino-1-(4-morpholinophenyl)butanone (trade name: Irgacure 369, manufactured by BASF SE) is preferable. When the pixel is formed by using the resist composition of the present invention, in a case where an electron beam is used, the photopolymerization initiator is not necessarily required.

In addition, in a case where the resist composition of the present invention is the positive-type resist composition, a photoacid generator may be added, if necessary. As the photoacid generator, a known photoacid generator such as a salt of an onium ion such as a sulfonium, iodonium, selenium, ammonium, or phosphonium ion, and an anion can be used.

Examples of the sulfonium ion can include the following: triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Examples of the iodonium ion can include diphenyliodonium, di-p-tolyliodonium, bis(4-dodecylphenyl)iodonium, bis(4-methoxyphenyl)iodonium, and (4-octyloxyphenyl)phenyliodonium.

An example of the selenium ion can include the following: triarylselenium such as triphenylselenium, tri-p-tolylselenium, tri-o-tolylselenium, tris(4-methoxyphenyl)selenium, 1-naphthyldiphenylselenium, tris(4-fluorophenyl)selenium, tri-1-naphtylselenium, or tri-2-naphthylselenium.

An example of the ammonium ion can include the following: tetraalkylammonium such as tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, or trimethylisobutylammonium.

Examples of the phosphonium ion can include the following: tetraphenylphosphsphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

Examples of the anion can include the following: a perhalogen acid ion such as $ClO_4^-$ or $BrO_4^-$; a halogenated sulfonic acid ion such as $FSO_3^-$ or $ClSO_3^-$; a sulfuric acid ion such as $CH_3SO_4^-$, $CF_3SO_4^-$, or $HSO_4^-$; a carbonic acid ion such as $HCO_3^-$ or $CH_3CO_3^-$; an aluminic acid ion such as $AlCl_4^-$ or $AlF_4^-$; a hexafluoro bismuthic acid ion; a carboxylic acid ion such as $CH_3COO^-$, $CF_3COO^-$, $C_6H_5COO^-$, $CH_3C_6H_4COO^-$, $C_6F_5COO^-$, or $CF_3C_6H_4COO^-$; an aryl boric acid ion such as $B(C_6H_5)_4^-$ or $CH_3CH_2CH_2CH_2B(C_6H_5)_3^-$; a thiocyanate ion; and a nitric acid ion. However, the present invention is not limited thereto.

[Medium]

In the resist composition of the present invention, as the medium used to dissolve or disperse the compound of the present invention, the binder resin, and the photopolymerizable monomer, the photopolymerization initiator, and the photoacid generator to be added, if necessary, water or an organic solvent can be used. Examples of the organic solvent can include the following: cyclohexanone, ethyl cellosolve acetate, butyl cellosolve acetate, 1-methoxy-2-propyl acetate, diethylene glycol dimethyl ether, ethylbenzene, 1,2, 4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropanol, butanol, methyl isobutyl ketone, and a petroleum solvent. These organic solvents may be used alone or in combination of two or more thereof.

[Coloring Agent]

In the coloring agent constituting the resist composition of the present invention, although the compound represented by Formula (1) is used, the compounds may be used alone or in combination of two or more thereof. In addition, in order to obtain desired spectral characteristics, another dye may be used together for color tone adjustment. The dye that can be used together is not particularly limited, but examples thereof can include the following: a condensed azo compound, an azo metal complex, a diketo pyrrolo pyrrole compound, an anthraquinone compound, a quinacridone compound, a naphthol compound, a benzimidazolon compound, a thioindigo compound, a perylene compound, a methine compound, an allylamide compound, and a base dye lake compound.

In addition to the additive, to the resist composition for a color filter of the present invention, an ultraviolet absorber or a silane coupling agent which is used to improve the adhesion to a glass substrate in production of a filter may be added, if necessary.

The disperser is not particularly limited, but a media type disperser such as a rotating shear type homogenizer, a ball mill, a sand mill, or an attritor, or a high-pressure counter collision type disperser can be used.

As described above, since the resist composition for a color filter of the present invention contains the compound represented by Formula (1), it is possible to obtain a resist composition for a color filter having high light fastness and excellent storage stability. In a color filter in which two or more kinds of pixels having different spectral characteristics are arranged adjacent to each other, the resist composition of the present invention is used for a pixel which forms at least one color among a plurality of pixel colors (for example, red, green, and blue). By doing so, it is possible to obtain a color filter having high light fastness and excellent storage stability.

<Toner>

Next, the toner according to the present invention will be described. Since the compound of the present invention has high light fastness and excellent storage stability, the compound can be preferably used for the toner.

The toner of the present invention contains the compound represented by Formula (1) as a coloring agent, a binder resin, and if necessary, a pigment for a toner used in the related art, a magnetic material, a wax, a charge control agent, and other additives. Examples of a method of producing a toner particle constituting the toner of the present invention can include a pulverization method, a suspension polymerization method, a suspension granulation method, an emulsion polymerization method, and an emulsion aggregation method. In addition, the toner of the present invention can also be used as a developer used in a liquid development method. Among them, the toner of the present invention in which the compound represented by Formula (1) is used as a coloring agent is preferably a pulverized toner produced by a pulverization method.

In the coloring agent, although the compound represented by Formula (1) is used, the compounds may be used alone or in combination of two or more thereof. In addition, in order to adjust a tone and the like according to the method of producing a toner, a known pigment or dye can be used together.

Next, an example of the method of producing a pulverized toner will be described.

[Method of Producing Pulverized Toner]

A coloring agent or the like is melted and kneaded in a binder resin and then uniformly dispersed, the melted and kneaded product is cooled and solidified, the kneaded product is finely pulverized with a fine pulverizer, and the finely pulverized product is classified with a classifier to obtain a toner particle having a desired particle diameter, thereby producing a pulverized toner. Specifically, first, the compound represented by Formula (1) as a coloring agent, a binder resin, and if necessary, a material such as a pigment for a toner used in the related art, a magnetic material, a wax, a charge control agent, or other additives are sufficiently mixed with each other with a mixer such as a Henschel mixer or a ball mill. Subsequently, the mixture is melted with a thermal kneader such as a roll, a kneader, or an extruder. Furthermore, the resins are dissolved to each other by kneading and then dispersed by adding a wax or a magnetic material, if necessary. In addition, a pulverized toner can be obtained by performing cooling and solidification and then performing pulverization and classification. In the production of the pulverized toner, a known production apparatus such as a mixer, a thermal kneader, or a classifier can be used. Hereinafter, the respective components constituting the toner will be described.

[Coloring Agent]

In the coloring agent, a pigment (for example, C.I. Pigment Blue 15:3 or the like) for a toner used in the related art and the compound represented by Formula (1) are used. As described above, these compounds may be used alone or in combination of two or more thereof. In addition, if necessary, a coloring agent such as a known dye or pigment can be used together.

In the case of using the pigment, the compound represented by Formula (1) can be used in a range of 0.01 to 1.0 time by mass, preferably in a range of 0.03 to 0.5 times by mass, and in particular, in a range of 0.05 to 0.2 times by mass, with respect to the pigment used together.

The coloring agent that can be used together is not particularly limited, but examples thereof can include the following: a condensed azo compound, an azo metal complex, a diketo pyrrolo pyrrole compound, an anthraquinone compound, a quinacridone compound, a naphthol compound, a benzimidazolon compound, a thioindigo compound, a perylene compound, a methine compound, an allylamide compound, and a base dye lake compound.

[Binder Resin]

Examples of the binder resin used in the toner of the present invention can include the following: a vinyl-based resin, a polyester-based resin, an epoxy-based resin, a polyurethane-based resin, a polyvinyl butyral-based resin, a terpene-based resin, a phenolic resin, an aliphatic or alicyclic hydrocarbon resin, and an aromatic petroleum resin. Furthermore, examples thereof can include a rosin and a modified rosin. Among them, a vinyl-based resin and a polyester-based resin are preferable from the viewpoint of chargeability or fixability. When the polyester-based resin is used, the effect of chargeability or fixability is further enhanced, which is more preferable. These resins may be used alone or in combination of two or more thereof. When two or more resins are used in combination, in order to control viscoelastic properties of the toner, resins having different molecular weights are preferably mixed with each other.

A glass transition temperature (Tg) of the binder resin is preferably 45 to 80° C., and more preferably 55 to 70° C. In addition, a number average molecular weight (Mn) of the binder resin is preferably 1,500 to 50,000, and a weight average molecular weight (Mw) of the binder resin is preferably 6,000 to 1,000,000.

When a polyester-based resin is used as a binder resin, although it is not particularly limited, but a molar ratio of an alcohol component/an acid component in the entire component is preferably 45/55 to 55/45. In the polyester-based resin, when the number of terminal groups of molecular chains is increased, an environmental dependence of the chargeability of the toner is increased. Therefore, an acid value is preferably 90 mgKOH/g or less, and more preferably 50 mgKOH/g or less. In addition, a hydroxyl value is preferably 50 mgKOH/g or less, and more preferably 30 mgKOH/g or less.

[Wax]

To the toner of the present invention, if necessary, a wax may be added. Examples of the wax can include a polyethylene wax, a paraffin wax, and a fatty acid ester wax, but are not limited thereto.

[Charge Control Agent]

To the toner of the present invention, if necessary, a charge control agent may be added. The charge control agent is not particularly limited, but examples of a charge control agent which controls the toner to have a negative charge can include the following: a polymer or a copolymer having a sulfonic acid group, a sulfonate group, or a sulfonic acid ester group, a salicylic acid derivative or metal complexes thereof, a monoazo metal compound, an acetylacetone metal compound, an aromatic oxycarboxylic acid, an aromatic mono- or polycarboxylic acid or metal salts thereof, anhydrides, esters, a phenol derivative such as bisphenol, a urea derivative, a metal-containing naphthoic acid-based compound, a boron compound, a quaternary ammonium salt, a calixarene, and a resin-based charge control agent.

In addition, examples of a charge control agent which controls the toner to have a positive charge can include the following: nigrosine and a nigrosine-modified product with a fatty acid metal salt, a guanidine compound, an imidazole compound, a quaternary ammonium salt such as tributylbenzylammonium-1-hydroxy-4-naphthosulfonate or tetrabutylammonium tetrafluoroborate, and an onium salt such as a phosphonium salt which is an analogue thereof and lake pigments thereof, a triphenylmethane dye and lake pigments thereof (as a laking agent, for example, phosphotungstic acid, phosphomolybdic acid, phosphotungstic molybdic acid, tannic acid, lauric acid, gallic acid, ferricyanide, and ferrocyanide), a metal salt of higher fatty acid, diorganotin oxide such as dibutyl tin oxide, dioctyl tin oxide, or dicyclohexyl tin oxide, diorganotin borates such as dibutyl tin borate, dioctyl tin borate, and dicyclohexyl tin borate, and a resin-based charge control agent.

These charge control agents may be used alone or in combination of two or more thereof.

EXAMPLES

Hereinafter, although the present invention will be described in more detail with reference to examples and comparative example, the technical scope of the present invention is not limited to these examples. In the description, "part(s)" and "%" represent "part(s) by mass" and "mass %" unless otherwise stated. In addition, an obtained compound was identified using a $^1$H nuclear magnetic resonance spectroscopic analysis ($^1$H-NMR) apparatus (AVANCE-600 NMR spectrometer, manufactured by BRUKER) and a MALDI-TOF/MS (MALDI-TOF/MS ultraFleXtreme, manufactured by BRUKER).

Production Example 1: Production of Compound (A2)

To a glacial acetic acid (20 mL) solution of N-butyl-N-phenylaniline (2.23 g), 2-sulfobenzaldehyde sodium (0.98 g) was added, and heating was performed at 100° C. for 5 hours. After the reaction was terminated, the reaction solution was cooled to room temperature, diluted with water (50 mL), and subjected to extraction using chloroform (50 mL). The extracted solution was concentrated under a reduced pressure and dissolved in ethyl acetate (20 mL), chloranil (2.33 g) was added thereto, and heating was performed at 80° C. for 4 hours. After the reaction was terminated, the reaction solution was filtered, and the resultant filtrate was washed with water three times. The resultant solution was purified by column chromatography to obtain a compound (A2) (1.82 g).

The compound was identified by [1] $^1$H-NMR analysis and [2] MALDI-TOF/MS analysis. The analysis results are shown below.

[1] Results of $^1$H-NMR (600 MHz, solvent: CDCl$_3$, room temperature: 25° C.):

δ (ppm)=8.47 (1H, d), 7.65 (1H, dd), 7.58 (8H, m), 7.52 (2H, dd), 7.46 (1H, dd), 7.33 (4H, d), 7.03 (1H, d), 6.77 (4H, d), 3.88 (4H, m), 1.78 (8H, m), 1.02 (6H, m)

[2] Results of MALDI-TOF/MS analysis: m/z=617.62 (M+H)$^+$ (Production Examples 2 to 15: Production of Other Compounds)

Compounds shown in Table 1 were produced and identified in the same manner as that of Production Example 1.

<Production of Ink>

An ink of the present invention and a comparative ink were produced by the following method.

Example 1: Production of Ink (1)

To a mixed solution of 45 parts of methyl ethyl ketone/45 parts of toluene, 5 parts of a polyvinyl butyral resin (Denka 3000-K, manufactured by Denka Company Limited) were gradually added and dissolved. Here, 5 parts of the compound (A2) synthesized in Production Example 1 were added and dissolved, thereby obtaining an ink (1).

Examples 2 to 13: Production of Inks (2) to (13)

Inks (2) to (13) were produced in the same manner as that of Example 1, except that, in Example 1, the compound (A2) was changed to compounds shown in Table 1.

Comparative Examples 1 to 4: Production of Comparative Inks (1) to (4)

Comparative inks (1) to (4) were produced in the same manner as that of Example 1, except that, in Example 1, the compound (A2) was changed to the following comparative compounds (B1) to (B4).

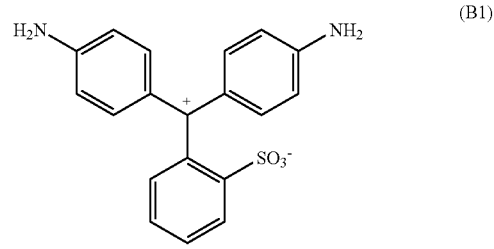

(B1)

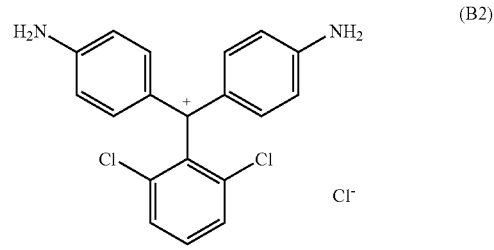

(B2)

-continued

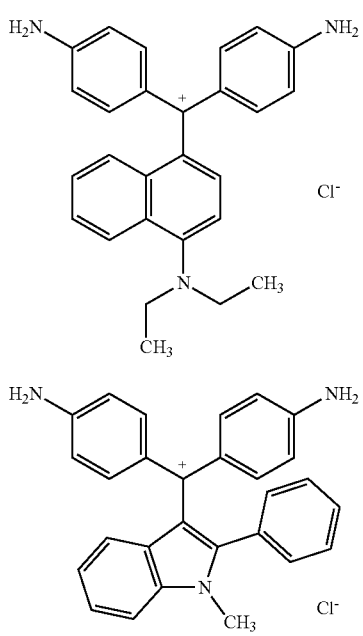

(B3)

(B4)

[Production of Sheet for Heat-Sensitive Transfer Recording and Image Sample]

The cyan ink (1) was applied to a polyethylene terephthalate film having a thickness of 4.5 μm (Lumirror (registered trademark), manufactured by TORAY INDUSTRIES, INC.) to have a thickness of 1 μm after drying and then dried, thereby preparing a sheet for heat-sensitive transfer recording by using the ink of the present invention.

The formed sheet for heat-sensitive transfer recording was transferred onto photographic paper by using a modified Selphy, thereby preparing an image sample (1).

[Light Fastness Evaluation]

The image sample was injected to a xenon tester (Atlas Weather-Ometer Ci4000, manufactured by Toyo Seiki Seisaku-sho, Ltd.), and then exposed under conditions (illuminance: 0.28 W/m² at 340 nm, black panel temperature: 40° C., and relative humidity: 50%) for 20 hours. When an initial optical concentration was set as $OD_0$ and O.D. after the exposure for 20 hours was set as $OD_{20}$, an O.D. residual rate was defined as follows.

O.D. residual rate (%)=($OD_{20}/OD_0$)×100

The evaluation criteria are as follows.
A: 70≤O.D. residual rate (%)
B: 60≤O.D. residual rate (%)<70
C: O.D. residual rate (%)<60

The obtained results are shown in Table 1. When the O.D. residual rate was 60 or higher, it was determined as a level at which the effects of the present invention were obtained.

[Evaluation of Storage Stability of Ink]

The ink of the example was sealed and stored at 10° C. for one month, and then the presence or absence of an aggregate after storage was visually observed. The observation results are shown in Table 1.

The evaluation criteria are as follows.
A: Almost no aggregate of the compound was observed (very excellent in the storage stability).
B: A small amount of aggregate of the compound was observed (excellent in the storage stability).
C: A considerable amount of aggregate of the compound was observed (inferior in the storage stability).

TABLE 1

| | Compound | Use | O.D. residual rate (%) | Determination of light fastness | Determination of storage stability |
|---|---|---|---|---|---|
| Example 1 | A2 | Ink (1) | 78 | A | A |
| Example 2 | A19 | Ink (2) | 87 | A | A |
| Example 3 | A24 | Ink (3) | 95 | A | B |
| Example 4 | A26 | Ink (4) | 83 | A | A |
| Example 5 | A28 | Ink (5) | 76 | A | A |
| Example 6 | A40 | Ink (6) | 89 | A | A |
| Example 7 | A64 | Ink (7) | 92 | A | A |
| Example 8 | A94 | Ink (8) | 62 | B | A |
| Example 9 | A98 | Ink (9) | 72 | A | A |
| Example 10 | A99 | Ink (10) | 96 | A | B |
| Example 11 | A100 | Ink (11) | 89 | A | A |
| Example 12 | A101 | Ink (12) | 91 | A | A |
| Example 13 | A102 | Ink (13) | 92 | A | A |
| Comparative Example 1 | B1 | Comparative ink (1) | 51 | C | C |
| Comparative Example 2 | B2 | Comparative ink (2) | 26 | C | C |
| Comparative Example 3 | B3 | Comparative ink (3) | 27 | C | C |
| Comparative Example 4 | B4 | Comparative ink (4) | 42 | C | C |

As shown in Table 1, it was found that in the ink of the example containing the compound represented by Formula (1), the light fastness was high and storage stability was excellent as compared with the comparative ink.

<Production of Color Filter>

The resist composition for a color filter and a color filter were produced by a method described below.

Example 14

With 12 parts of the compound (A2) synthesized in Production Example 1, 120 parts of cyclohexanone were mixed, and the mixture were dispersed with an attritor (manufactured by Mitsui Mining Co., Ltd.) for 1 hour, thereby obtaining an ink (1) for a resist composition.

Subsequently, 22 parts of the ink (1) for a resist composition were slowly added to a mixed solution of the following materials and stirring was performed at room temperature for 3 hours.

Acrylic copolymer obtained by performing synthesis at a monomer ratio of 40 mass % of n-butyl methacrylate, 30 mass % of acrylic acid, and 30 mass % of hydroxyethyl methacrylate (weight average molecular weight Mw: 10,000) 6.7 parts
Dipentaerythritol pentaacrylate 1.3 parts
2-Benzyl-2-dimethylamino-1-(4-morpholinophenyl)-butanone (photopolymerization initiator) 0.4 parts
Cyclohexanone 96 parts These materials were filtered using a filter having a hole diameter of 1.5 μm to obtain a resist composition (1) for a color filter.

The resist composition (1) for a color filter was spin-coated on a glass substrate and dried at a temperature of 90° C. for 3 minutes, the entire surface was exposed and then subjected to post curing at a temperature of 180° C., thereby producing a color filter (1).

Examples 15 to 18

Resist compositions (2) to (5) for a color filter were produced in the same manner as that of Example 14, except that, the compound (A2) was changed to compounds shown in Table 2. In addition, color filters (2) to (5) were produced in the same operation as that of Example 14, except that the obtained resist compositions (2) to (5) for a color filter were used instead of the resist composition (1) for a color filter.

Comparative Examples 5 to 8

Resist compositions (1) to (4) for a comparative color filter were obtained in the same manner as that of Example 14, except that the compound (A2) was changed to comparative compounds (B1) to (B4). In addition, comparative color filters (1) to (4) were produced in the same operation as that of Example 14, except that the obtained resist compositions (1) to (4) for a comparative color filter were used instead of the resist composition (1) for a color filter.

[Light Fastness Evaluation]

The image sample was injected to a xenon tester (Atlas Weather-Ometer Ci4000, manufactured by Toyo Seiki Seisaku-sho, Ltd.), and then exposed under conditions (illuminance: 0.36 W/m² at 340 nm, black panel temperature: 50° C., and relative humidity: 50%) for 70 hours. When an initial optical concentration was set as $OD_0$ and O.D. after the exposure for 70 hours was set as $OD_{70}$, an O.D. residual rate was defined as follows.

O.D. residual rate (%)=($OD_{70}/OD_0$)×100

The evaluation criteria are as follows.
A: 50≤O.D. residual rate (%)
B: 35≤O.D. residual rate (%)≤50
C: O.D. residual rate (%)≤35

The obtained results are shown in Table 2. When the O.D. residual rate was more than 35, it was determined as a level at which the effects of the present invention were obtained.

[Evaluation of Storage Stability of Color Filter]

Each color filter was left at a temperature of 40° C./humidity of 80% for 7 days and then stored at a temperature of 10° C./humidity of 30% for one month, and then a surface state was observed by magnifying the surface 20 times with a phase-contrast microscope (trade name: BX53, manufactured by Olympus Corporation). The observation results are shown in Table 2.

The evaluation criteria are as follows.

A: Almost no aggregate of the compound was observed (very excellent in the storage stability).

B: A small amount of aggregate of the compound was observed (excellent in the storage stability).

C: A considerable amount of aggregate of the compound was observed (inferior in the storage stability).

TABLE 2

|  | Compound | Use | O.D. residual rate (%) | Determination of light fastness | Determination of storage stability |
| --- | --- | --- | --- | --- | --- |
| Example 14 | A2 | Color filter (1) | 53 | A | A |
| Example 15 | A19 | Color filter (2) | 65 | A | A |
| Example 16 | A64 | Color filter (3) | 72 | A | A |
| Example 17 | A94 | Color filter (4) | 42 | B | A |
| Example 18 | A102 | Color filter (5) | 75 | A | A |
| Comparative Example 5 | B1 | Comparative color filter (1) | 26 | C | C |
| Comparative Example 6 | B2 | Comparative color filter (2) | 12 | C | B |
| Comparative Example 7 | B3 | Comparative color filter (3) | 16 | C | C |
| Comparative Example 8 | B4 | Comparative color filter (4) | 19 | C | C |

<Production of Toner>

A toner was produced by a method described below.

Example 19

Binder resin (polyester resin): 100 parts by mass
(Tg: 55° C., acid value: 20 mgKOH/g, hydroxyl value: 16 mgKOH/g, main peak molecular weight: Mp 4,500, number average molecular weight Mn 2,300, weight average molecular weight Mw 38,000)
C.I. Pigment Blue 15:3 5 parts by mass
Compound (A40): 0.5 parts by mass
1,4-Di-t-butyl salicylic acid aluminum compound: 0.5 parts by mass
Paraffin wax (maximum endothermic peak temperature: 78° C.): 5 parts by mass These materials were sufficiently mixed with each other with a Henschel mixer (trade name: FM-75J type, manufactured by Mitsui Mining Co., Ltd.). Thereafter, kneading was performed with a twin-screw kneader (trade name: PCM-45 type, manufactured by Ikegai Ironworks Corp.) which was set at a temperature of 130° C. and in a Feed amount of 60 kg/hr. The temperature of a kneaded product during discharge was about 150° C. After the obtained kneaded product was cooled and then coarsely pulverized with a hammer mill, fine pulverization was performed in a Feed amount of 20 kg/hr with a mechanical pulverizer (trade name: T-250, manufactured by Turbo Kogyo Co., Ltd.). Furthermore, the obtained finely pulverized product was classified with a multi-division classifier using a Coanda effect, thereby obtaining a toner particle. A silica fine particle was added to 100 parts by mass of the obtained toner particle in an amount of 2 parts by mass using a Henschel mixer, thereby obtaining a toner (1). A weight average particle diameter (D4) of the obtained toner was about 6.0 μm, a rate of particles having a particle diameter of 4.1 μm or less was 31.0% in number, and a rate of particles having a particle diameter of 10.1 μm or more was 0.7 vol %.

A fixed image having a mounted amount of the toner of 0.45 mg/cm² was prepared on CLC color copy paper (manufactured by Canon Inc.) using a modified LBP-5300 (trade name, manufactured by Canon Inc.).

Alight fastness test as in Examples 1 to 10 was performed on the obtained image, and as a result, an O.D. residual rate (%) was 80% or higher.

In addition, 1 g of the toner was placed in a 10 cc resin cup, left at a temperature of 40° C./humidity of 80% for 7 days, and further left at a temperature of 10° C./humidity of 30% for one month. Thereafter, the presence or absence of an aggregate was examined. As a result, it was confirmed that almost no aggregate was observed and the storage stability was very excellent.

The compound of the present invention is a compound having high light fastness and excellent storage stability. The compound of the present invention can be preferably used for an ink, a resist composition for a color filter, a sheet for heat-sensitive transfer recording, and a coloring agent of a toner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A compound having a structure represented by formula (1):

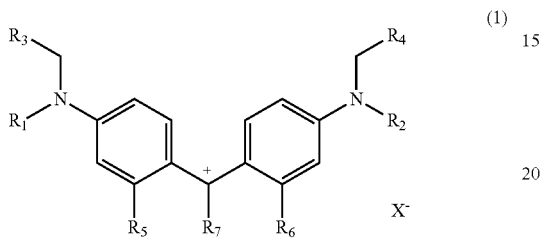

(1)

wherein, in the formula (1):
$R_1$ and $R_2$ each independently represent any one functional group selected from the group consisting of a 2,6-dichlorophenyl group, a 2,6-dichloro-4-butylphenyl group, and a 2,6-dichloro-4-butoxyphenyl group;
$R_3$ and $R_4$ each independently represent a C2-C12 alkyl group having a substituent or an unsubstituted C2-C12 alkyl group, a cyano group, a trifluoromethyl group, or a halogen atom;
$R_5$ and $R_6$ each independently represent a hydrogen atom or an alkyl group;
$R_7$ represents a structure represented by formula (2) or (3):

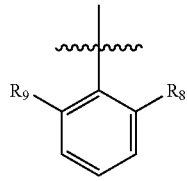

(2)

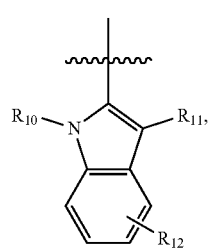

(3)

wherein, in the formula (2):
$R_8$ represents a —$SO_3^-$ group, an alkoxysulfonyl group, a sulfonic acid amide group, a halogen atom, a perfluoroalkyl group, or a nitro group; and
$R_9$ represents a hydrogen atom or a halogen atom, and
wherein, in the formula (3), $R_{10}$ to $R_{12}$ each independently represent a hydrogen atom, an alkyl group, or an aryl group having a substituent or an unsubstituted aryl group; and
$X^-$ represents an anion, and in a case where at least one anionic substituent is included in a molecule, $X^-$ may not be present.

2. The compound according to claim 1, wherein the formula (2) has a structure represented by formula (4):

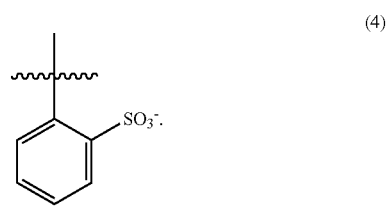

(4)

3. The compound according to claim 1, wherein the formula (1) is represented by any one of formulas (A19), (A24), (A40), (A94), and (A98) to (A102):

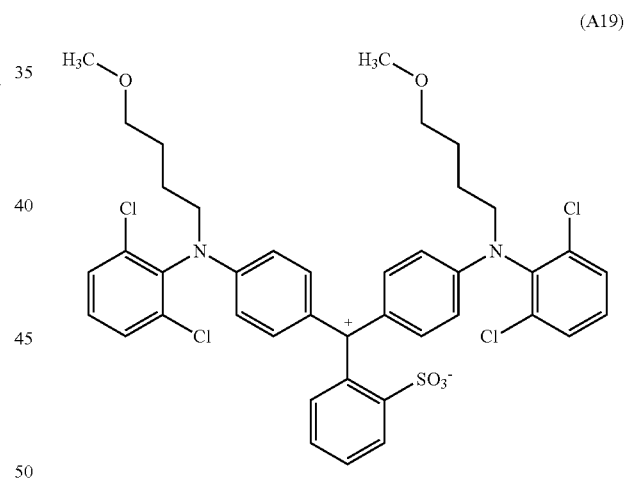

(A19)

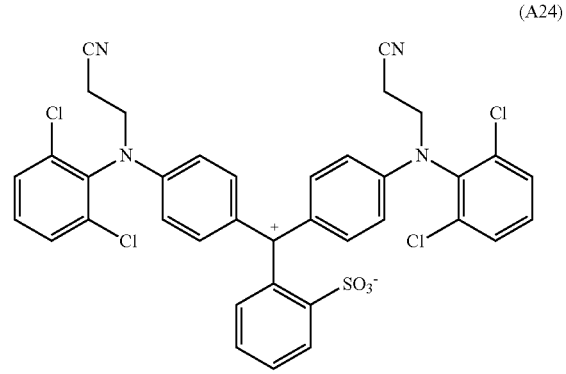

(A24)

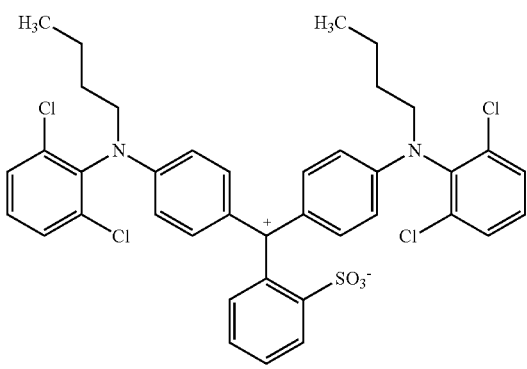 (A40)
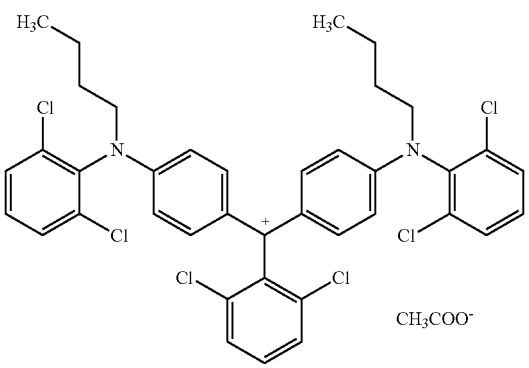 (A94)
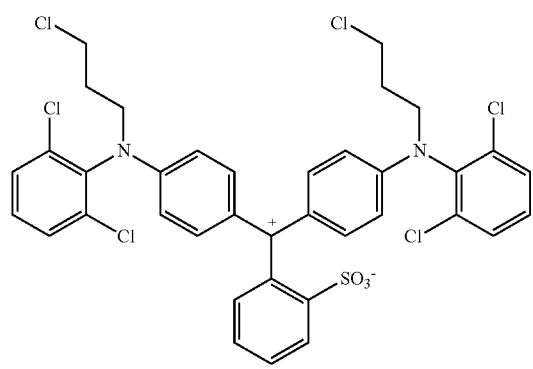 (A98)
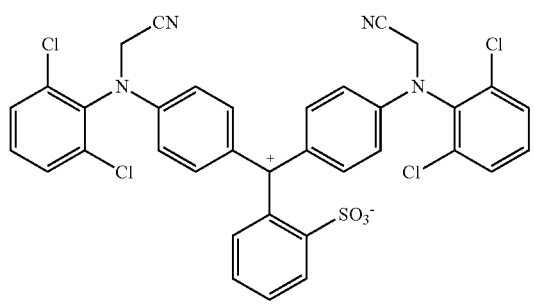 (A99)
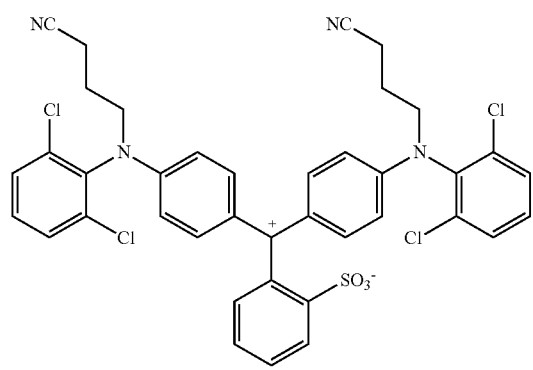 (A100)
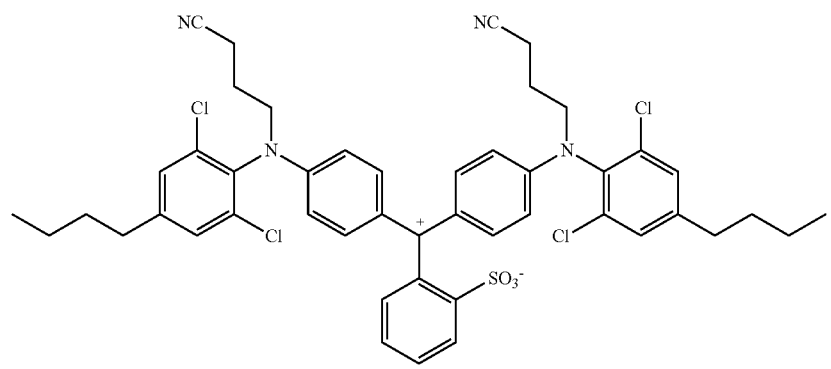 (A101)

-continued

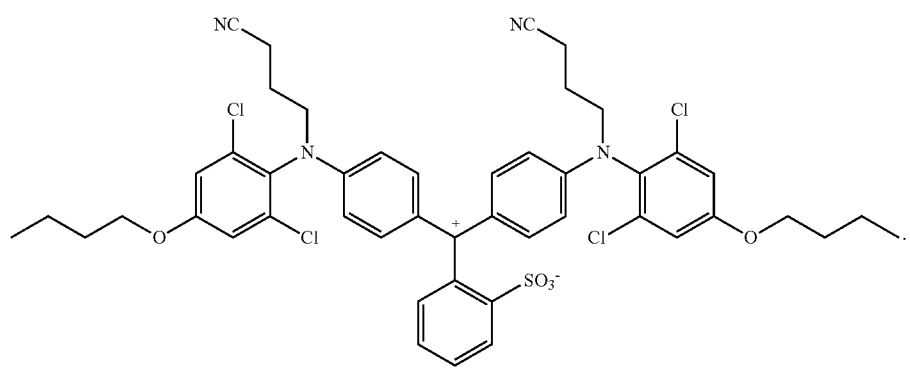

(A102)

4. An ink comprising:
a medium; and
a compound present in a dissolved or dispersed state in the medium,
wherein the compound is the compound according to claim 1.

5. A resist composition for a color filter comprising the compound according to claim 1.

6. A color filter comprising the compound according to claim 1.

7. A sheet for heat-sensitive transfer recording comprising:
a substrate; and
a coloring material layer formed on the substrate,
wherein the coloring material layer contains the compound according to claim 1.

8. A toner comprising:
a binder resin; and
a coloring agent,
wherein the coloring agent contains the compound according to claim 1.

* * * * *